US012754186B2

(12) United States Patent
De Sa Ferreira Facio et al.

(10) Patent No.: US 12,754,186 B2
(45) Date of Patent: Oct. 6, 2026

(54) MEANS AND METHODS FOR THE DIAGNOSIS, CLASSIFICATION AND/OR MONITORING OF PEDIATRIC TUMORS

(71) Applicants: Stichting EuroFlow, Leiden (NL); Academisch Ziekenhuis Leiden h.o.d.n. LUMC, Leiden (NL); University of Salamanca, Salamanca (ES)

(72) Inventors: Cristiane De Sa Ferreira Facio, Rio de Janeiro (BR); Vitor Dessanti Botafogo Gonçalves, Salamanca (ES); Elaine Sobral Da Costa, Rio de Janeiro (BR); Jacobus Johannes Maria Van Dongen, Leiden (NL); José Alberto Orfao De Matos Correia E Vale, Salamanca (ES)

(73) Assignees: Stichting EuroFlow, Leiden (NL); Academisch Ziekenhuis Leiden h.o.d.n. LUMC, Leiden (NL); University of Salamanca, Salamanca (ES)

( * ) Notice: Subject to any disclaimer, the term of this patent is extended or adjusted under 35 U.S.C. 154(b) by 822 days.

(21) Appl. No.: 17/926,910

(22) PCT Filed: Jun. 9, 2021

(86) PCT No.: PCT/NL2021/050367
§ 371 (c)(1),
(2) Date: Nov. 21, 2022

(87) PCT Pub. No.: WO2021/251824
PCT Pub. Date: Dec. 16, 2021

(65) Prior Publication Data

US 2024/0248091 A1 Jul. 25, 2024

(30) Foreign Application Priority Data

Jun. 10, 2020 (EP) .................................... 20179302

(51) Int. Cl.
*G01N 33/575* (2026.01)
*G01N 33/49* (2006.01)
*G01N 33/569* (2006.01)

(52) U.S. Cl.
CPC ..... *G01N 33/5759* (2026.01); *G01N 33/4915* (2013.01); *G01N 33/56972* (2013.01); *G01N 2333/705* (2013.01)

(58) Field of Classification Search
CPC ....... G01N 33/57492; G01N 33/57496; G01N 33/57407; G01N 2333/705; G01N 2800/38; G01N 33/57557; G01N 33/5759; G01N 33/56972; G01N 33/4915
See application file for complete search history.

(56) References Cited

PUBLICATIONS

Tembhare et al. Utility of flow cytometric detection of circulating tumor cells (CTC) in the prediction of bm metastasis in children with neuroblastoma. Pedriatric Blood and Cancer 65, Supp. Supplement pp. S281. Abstract No. PO-415 (Nov. 2018)—Abstract.*
Ferreira Facio et al. Contribution of Multiparameter Flow Cytometry Immunophenotyping to the Diagnostic Screening and Classification of Pediatric Cancer. PLOS One 8: (3): e55534-e55535 (Mar. 2013).*
Cristiane S. Ferreira-Facio, et al., "Contribution of Multiparameter Flow Cytometry Immunophenotyping to the Diagnostic Screening and Classification of Pediatric Cancer", Plos One, vol. 8, No. 3, May 3, 2013.
Matthew C. Hiemenz, et al., "Oncokids A Comprehensive Next-Generation Sequencing Panel for Pediatric Malignancies", Journal of Molecular Diagnostics, vol. 20, No. 6, Nov. 2018, pp. 765-776.
Anil Handoo, et al., "Flow Cytometry in Pediatric Malignancies", Indian Pediatrics, Indian Pediatric, Calcutta, IN, vol. 55, No. 1, Mar. 14, 2018, pp. 55-62.
D. McKay, "Gene chips accurately diagnose four complex childhood cancers," Trends in Biotechnology, Elsevier Publications, Cambridge, GB, vol. 19, No. 8, Aug. 1, 2001, p. 285.

* cited by examiner

*Primary Examiner* — Gailene Gabel
(74) *Attorney, Agent, or Firm* — Hoffmann & Baron LLP

(57) ABSTRACT

A kit-of-parts for the flow cytometric detection of pediatric tumor cells, comprising fluorochrome-conjugated antibodies directed against the cell surface markers CD45, CD56, GD2, CD99, CD8, EpCAM, CD4, smCD3, CD19 and CD271, the cytoplasmic marker cyCD3, and the nuclear marker(s) numyogenin and/or nuMyoD1, wherein (i) the antibodies against the markers CD99/CD8 are conjugated to the same fluorochrome and representing a first marker pair CD99/CD8;
(ii) the antibodies against the markers EpCAM/CD4 are conjugated to the same fluorochrome and representing a second marker pair EpCAM/CD4;
(ii) the antibody against CD271 is conjugated to the same fluorochrome as the antibody against either cyCD3 or smCD3 and representing a third marker pair CD271/cyCD3 or CD271/smCD3;

wherein between the first, second and third marker pairs the fluorochromes are distinguishable; and wherein the antibodies against the cytoplasmic and the nuclear markers are physically separated from the antibodies against the cell surface markers.

17 Claims, 3 Drawing Sheets

A)
B)
C)
D)
E)
F)
G)
H)
G1
G2
G3
G1A
G1B
G1C
G1D
SSC-A
CD45
CD19/cyCD3
smCD3
Total B lymphocytes
Plasma cells
B lymphocytes
CD4⁺ T-cells
CD4⁺ CD8⁺ T-cells
CD8⁺ T-cells
CD4⁻ CD8⁻ T-cells
NK-cells
eosinophils
neutrophils
Monocytes and dendritic cells

MEANS AND METHODS FOR THE DIAGNOSIS, CLASSIFICATION AND/OR MONITORING OF PEDIATRIC TUMORS

CROSS-REFERENCE TO RELATED APPLICATIONS

This application is a national stage application under 35 U.S.C. § 371 of international patent application PCT/NL2021/050367, filed on Jun. 9, 2021, which claims priority from EP 20179302.3, filed on Jun. 10, 2020, which are incorporated herein by reference.

TECHNICAL FIELD

The invention relates to the field of medical diagnostics. In particular, it relates to diagnosis of pediatric tumors using flow cytometry.

BACKGROUND OF THE DISCLOSURE

The invention provides methods and reagents for the detection and monitoring of pediatric tumors by multiparameter flow cytometry (MFC) using a single tube. Also provided are tools for the simultaneous characterization of tumor infiltrating lymphocytes (TILs) and tumor infiltrating monocytes/dendritic cells (TIM) that infiltrate the tumor tissues. In addition to the detection and characterization of the tumor cells in primary tumor sites, a reagent composition of the invention also allows for detection of tumor cells in tissues other than the primary tumor through analysis of peripheral blood, bone marrow, cerebrospinal fluid, metastatic tumor tissues and any other tissue samples from the patients, and the evaluation of treatment effectiveness. Kits and methods relating to the reagent composition are also provided.

Pediatric solid tumors comprise a heterogeneous group of diseases that predominantly occur in the age range of 0-15 years. Worldwide, it is estimated an incidence of more than 175,000 cases per year and a mortality rate of 96,000 children per year. Solid tumors account for roughly 75% of all childhood cancers and they comprise lymphomas, central nervous system (CNS) tumors, neuroblastoma, soft tissue sarcomas, nephroblastoma, bone tumors, retinoblastoma, hepatoblastoma, germ-cell tumors and carcinomas (Ward E, CA Cancer J CLIN 2014; 64:83).

Correct diagnosis of pediatric cancer is known to be complex and difficult. Although classical histological features are generally highly suggestive of specific tumor types, most pediatric tumors may be indistinguishable by light microscopy and immunohistochemistry only. Early accurate diagnosis, classification and risk-stratification are crucial in children with cancer, particularly because distinct diagnostic entities require different and highly specific therapies.

Currently, conventional procedures used for the diagnostic screening and classification of pediatric solid tumors rely on morphological and immunohistochemical analysis of formalin-fixed, paraffin-embedded solid tumor specimens. The majority of pediatric solid tumors are classified under the descriptive category of “small round cell tumors”. Small round cell tumors include tumors formed by undifferentiated, small-sized cells with scanty cytoplasm and round hyperchromatic nuclei. Due to the fact that these tumors show similar morphological features by light microscopy, precise diagnosis of pediatric solid tumors is often challenging, with the possibility of misdiagnosis, in the absence of further analyses (Magro G, Acta Histochem. 2015; 117:397)

Thus, further immunohistochemical studies are mandatory. Despite this, there is not a uniformly recommended panel of antibodies that could be applied in such immunohistochemical analyses for highly sensitive and specific diagnosis and classification of the majority of childhood cancer subtypes. Even more, no technical solution is currently available or has been described based on immunohistochemistry or flow cytometry, for simultaneous assessment of all informative markers for direct tumor diagnosis and classification.

Therefore, in contrast to the diagnostic work-up of pediatric leukemias where MFC immunophenotyping is essential for rapid diagnosis, classification and monitoring of the disease, MFC immunophenotyping is not routinely used for the diagnostic work-up of pediatric solid tumors. In fact, MFC immunophenotyping has so far been restricted to the evaluation of a limited number of markers for the identification of specific diagnostic entities including those expressing highly characteristic phenotypes, such as the CD45−CD56+ phenotypic profile in neuroendocrine tumors (Bryson G J, J Clin Pathol. 2002; 55:535) the CD45−CD56+GD2+ immunophenotype of neuroblastoma (Bozzi F, Anticancer Res.2006; 26:3281), the CD57+CD56+CD99+CD45− features in primitive neuroectodermal tumors (Dubois SG, Pediatr Blood Cancer.2010; 54:13) and the CD45−CD56+ nuMyogenin+ profile in rhabdomyosarcoma (Almazán-Moga A,. Cytometry A. 2014; 85:1020).

However, despite these phenotypic profiles allegedly being characteristic of specific diagnostic entities among pediatric cancer, they have systematically shown a relatively low efficiency when prospectively tested in the clinical settings against conventional diagnostic procedures, based on panels of 4-6-color antibody combinations, due to their inability to accurately differentiate among different tumor types. In addition, diagnostic MFC analyses of childhood solid tumor tissues did not provide simultaneous information about the type and number of tumor infiltrating inflammatory and immune cells that coexist within the tumor in the same sample.

In 2013, Ferreira-Facio et al (Ferreira-Facio, PLOS One. 2013; 8: e55534) investigated the staining pattern of tumor cells from 52 pediatric solid tumors by MFC immunophenotyping using a larger panel of antibody combinations that contained 33 distinct antibody specificities in multiple tubes of up to 8-colors. In the above study, all reactive/inflammatory samples classified as such by conventional histopathological criteria were also correctly diagnosed by MFC alone. Similarly, in all but two uncommon lymphoma samples, tumor cells were detected by MFC. Based on this study, it was concluded that combined assessment of CD45, CD56, CD81, CD99, EpCAM, GD2, nuclear nuMyoD1, nuMyogenin and CD271, in addition to other specific B-cell and T-cell markers, could be a useful antibody panel for both tumor diagnosis and classification. However, the authors failed to provide a way to combine all informative markers in a single antibody combination, that would allow both: i) identification of pediatric cancer tumor cells; ii) their diagnostic classification and iii) detailed analysis of the tumor infiltrating immune cells coexisting in the same sample. In addition, they systematically failed on identifying some tumor subtypes such as Hodgkin Lymphoma.

In parallel, in WO2010/140885 van Dongen et al. reported a panel of antibody reagents conjugated with fluorescent compounds to be used for the immunophenotypic characterization of normal, reactive, regenerating and neoplastic leukocyte cell populations. However, such panel of antibody combinations is fully restricted to leukemia and lymphoma patients, and no similar attempt has been made in pediatric cancer as regards the diagnosis, classification and monitoring of non-hematopoietic solid tumors vs hematological malignancies (e.g. pediatric lymphoma).

SUMMARY OF THE DISCLOSURE

Thus, the present inventors set out to design a single combination of antibody reagents that allows for the systematic identification and classification of tumor cells in pediatric solid tumor samples and simultaneously provides detailed characterization of the infiltrating immune cells coexisting in the same sample. Furthermore, they aimed at providing a MFC protocol that includes a single and unique combination of antibody reagents for the diagnostic screening and classification of solid tumors in pediatric patients and simultaneous detailed analysis of the immune cell microenvironment of the tumor.

These goals were surprisingly met by the development of a novel ≥8-color/fluorochrome antibody combination for the simultaneous detection of ≥12 different proteins that show variable but characteristic expression profiles in individual tumor cells present in childhood solid tumor samples, and allows for the identification and classification of pediatric cancer into different diagnostic entities and simultaneous assessment of the tumor infiltrating immune cells. More in particular, it was found that this can be achieved by the staining for (i) the cell surface markers CD45, CD56, GD2, CD99, CD8, EpCAM, CD4, smCD3, CD19 and CD271; (ii) the cytoplasmic marker cyCD3; and (iii) the nuclear marker (s) nuMyogenin and/or nuMyoD1, wherein the antibodies against the markers CD99/CD8 are conjugated to a first fluorochrome and representing a first marker pair CD99/CD8; the antibodies against the markers EpCAM/CD4 are conjugated to a second fluorochrome and representing a second marker pair EpCAM/CD4, and the antibody against CD271 is conjugated to a third fluorochrome as the antibody against either cyCD3 or smCD3 and representing a third marker pair CD271/cyCD3 or CD271/smCD3. In order to allow for a stepwise staining for the cell surface markers on intact cells in an aliquot of a test sample, followed by permeabilization of the same aliquot, and staining for intracellular and nuclear markers, the antibodies against the cytoplasmic and the nuclear markers are physically separated from (i.e. not mixed with) the antibodies against the cell surface markers.

The invention therefore relates to a kit-of-parts for the flow cytometric detection of pediatric tumor cells, the kit comprising fluorochrome-conjugated antibodies directed against the cell surface markers CD45, CD56, GD2, CD99, CD8, EpCAM, CD4, smCD3, CD19 and CD271, the cytoplasmic marker cyCD3, and the nuclear marker(s) nuMyogenin and/or nuMyoD1, wherein (i) the antibodies against the markers CD99/CD8 are conjugated to the same fluorochrome and representing a first marker pair CD99/CD8:

(ii) the antibodies against the markers EpCAM/CD4 are conjugated to the same fluorochrome and representing a second marker pair EpCAM/CD4, (ii) the antibody against CD271 is conjugated to the same fluorochrome as the antibody against either cyCD3 or smCD3 and representing a third marker pair CD271/cyCD3 or CD271/smCD3;

wherein the kit comprises antibodies conjugated to ≥8 distinguishable fluorochromes (at least an 8-color antibody combination);

and wherein between the first, second and third marker pairs the fluorochromes are distinguishable; and wherein the antibodies against the cytoplasmic and the nuclear markers are physically separated from the antibodies against the cell surface markers.

This kit for the staining of an aliquot of a single cell suspension contains a unique panel of fluorochrome-conjugated antibodies combination against a set of 12 "backbone markers", wherein antibodies against certain selected markers are each conjugated to a unique, distinct fluorochrome, whereas antibodies against other selected markers are "paired", i.e. antibodies to different markers are conjugated to the same fluorochrome.

For example, in a kit of the invention, antibodies against the 4 selected markers CD45, CD56, GD2 and nuMyogenin are each conjugated to a distinct fluorochrome (i.e. fluorochromes 1 to 4, respectively), whereas antibodies against each of the marker pairs CD99/CD8, EpCAM/CD4, CD271/cy/smCD3 is combined with another, but distinct, fluorochrome (i.e. fluorochromes 5 to 8, respectively) (i.e. antibody combination 1 in Table 1).

Various kit designs comprising at least two containers (reagent tubes) are encompassed. For instance, the kit may contain more than two containers, the total number of containers comprising the unique antibody panel as provided herein. In one embodiment, the conjugated antibodies against the cell surface markers are divided over two or more containers. Likewise, the conjugated antibodies against the cytoplasmic marker cyCD3 and the nuclear marker(s) nuMyogenin and/or nuMyoD1 may be present in separate containers. For the sake of convenience, the kit preferably comprises a first reagent composition comprising a mixture of the conjugated antibodies against the cell surface markers CD45, CD56, GD2, CD99, CD8, EpCAM, CD4, smCD3, CD19 and CD271 contained in a first container, and a second reagent composition comprising the conjugated antibodies against the cytoplasmic marker cyCD3 and the nuclear marker(s) nuMyogenin and/or nuMyoD1, contained in a second container.

According to the invention, both the cytoplasmic (cy) and surface membrane (sm) version of CD3 are used as markers, and the marker CD271 is always paired with either cyCD or smCD3. The marker cyCD3 can either be a unique marker, or it can form a marker pair with CD271, while the marker smCD3 can form a marker pair with either CD271 or CD19.

In one embodiment, the kit-of-parts comprises antibodies against the third marker pair CD271/cyCD3, and the antibodies against the markers smCD3/CD19 are conjugated to the same fluorochrome to form a fourth marker pair smCD3/CD19, and wherein between different pairs the fluorochromes are distinguishable. See for example any one of combinations 1-3, 7-16 and 18-29 in Table 1. In another embodiment, the kit-of-parts comprises the third marker pair CD271/smCD3, and the antibodies against the markers CD19 and cyCD3 are each conjugated to a distinct fluorochrome. See for example any one of combinations 4-6, 17 and 30 in Table 1.

A kit of the invention is further characterized by the presence of antibodies against either one or both of the nuclear marker(s) nuMyogenin and nuMyoD1. In one embodiment, only the marker nuMyogenin is used. See for example any one of combinations 1, 4, 7, 9, 11, 13, 15, 18, 23-26 in Table 1. Thus, the 12 markers can be conjugated with a total of 9 fluorochromes: 6 markers (CD45, CD56, GD2, nuMyogenin, CD19 and cyCD3) are each conjugated to a distinct fluorochrome, and the other 6 markers are placed in pairs of antibodies (CD99/CD8, EpCAM/CD4 and smCD3/CD271) each pair being combined with a different fluorochrome. In another embodiment, only the marker nuMyoD1 is used. See for example any one of combinations 2, 5, 8, 10, 16, 17, 19, 21, 27, 29-30 in Table 1. In yet another embodiment, the invention provides a kit-of-parts comprising antibodies against the markers nuMyogenin and nuMyoD1, and wherein the antibodies against the markers nuMyogenin/nuMyoD1 are conjugated to the same fluorochrome to form a further marker pair nuMyogenin/nuMyoD1, and wherein between different pairs (i.e. the CD99/CD8 pair, the EpCAM/CD4 pair, the CD271/(cy/sm) CD3 and the nuMyogenin/nuMyoD1 pair) the fluorochromes are distinguishable. See for example any one of combinations 3, 6, 12, 14, 20, 22 and 28 in Table 1.

Further embodiments of this invention relate to any of the above antibody combinations that is expanded to include additional markers conjugated with up to five distinct, additional fluorochromes for a total of up to 12 to 14 different colors (i.e. fluorochromes), for further identification and characterization of Hodgkin lymphoma cells, germ cell tumors and/or bone tumors. For Hodgkin lymphoma cells, one or more markers might be selected from the following proteins: HLADR, CD30, CD71, CD40 and CD95. For further characterization of germ cell tumors, the OCT-3/4, BAP and/or PLAP markers might be used, whereas for bone tumors osteopontin and/or bone alkaline phosphatase might be used in addition to the previous 12 backbone markers.

Therefore, in some embodiment, a kit-of-parts according to the invention further comprises fluorochrome-conjugated antibodies against one or more of the Hodgkin lymphoma cell surface markers HLA-DR, CD30, CD71, CD40 and CD95. As is illustrated by the exemplary antibody combinations 11-14, 17-30 of Table 1, unique fluorophores are used for each of the further antibodie(s). In the kit, they may be suitably combined in admixture with the antibodies against the cell surface markers CD45, CD56, GD2, CD99, CD8, EpCAM, CD4, smCD3, CD19 and CD271.

Alternatively or additionally, a kit-of-parts according to the invention may further comprise fluorochrome-conjugated antibodies against one or more of the germ cell tumor cell surface markers OCT-3/4, BAP and PLAP. In one aspect, the kit comprises antibodies against the markers OCT-3/4 and PLAP, and wherein the antibodies against the markers OCT-3/4/PLAP are conjugated to the same fluorochrome to form a marker pair OCT-3/4/PLAP, and wherein between different pairs the fluorochromes are distinguishable.

See exemplary antibody combinations 7, 8, 25-29 of Table 1.

Alternatively or additionally, a kit-of-parts may further comprise fluorochrome-conjugated antibodies against one or both of the bone tumor cell surface markers osteopontin and bone alkaline phosphatase (BAP). In one aspect, the kit comprises antibodies against the markers osteopontin and BAP, and wherein the antibodies against the markers osteopontin/BAP are conjugated to the same fluorochrome to form a marker pair osteopontin/BAP, and wherein between different pairs the fluorochromes are distinguishable. See exemplary antibody combinations 7, 8, 21, 22, 24, 26-29 of Table 1.

In a specific embodiment, four Hodgkin lymphoma markers (i.e. HLADR, CD30, CD40 and CD95) plus one or a mixture of two or three of the above germ cell tumor markers (e.g. OCT-3/4, BAP and/or PLAP) plus one or both bone tumor markers are combined in six additional fluorochrome positions with the backbone markers listed in combinations 1, 3 and 5 (e.g. antibody combinations 18 to 29 in table 1).

Preferred aspects of the invention relate to a kit-of-parts comprising one or more antibody combination(s) selected from the antibody combinations 1 through 30 of Table 1.

Any of the above antibody combinations can be combined with a reagent for excluding debris and/or non-lysed cells, such as a dye capable of detecting nucleated cells. Hence, also provided is a kit-of-parts which further comprises a nucleated cell integrity dye.

The specific fluorochromes to which the antibodies for use in the invention are conjugated can be selected from the wide variety of fluorochromes that are known in the art, and/or from fluorochromes yet to be developed. In one embodiment, the following (groups of) fluorochromes or any other combination of fluorochromes and/or fluorochrome tandems is used that can be measured simultaneously in a >8-color flow cytometer:

i) Pacific Blue (PacB), brilliant violet (BV®) 421 (fluorescent polymer), Cascade blue CASCADE BLUE® (fluorescent dye), ALEXA FLUOR® (AF) 405 (fluorescent dye), EFLUOR® (EF) 450 (fluorescent dye), HORIZON® V450 (HV450) (fluorochrome), VIOBLUE (fluorescent dye), DYLIGHT®405 (fluorescent dye), SUPER BRIGHT® 436 (fluorescent polymer dye), BV®480;
ii) PACIFIC ORANGE® (PacO) (violet laser-excitable dye), OC515, BV®510, BV®480, CASCADE YELLOW® (fluorescent dye), BV®570, VIOGREEN® (fluorescent dye), ALEXA FLUOR® (AF) 430 (fluorescent dye), Ameyan AMCYAN® (fluorescent protein and cyan dye), HV500, KHROME ORANGE® (fluorochrome) (KO), Brilliant Ultra Violet BUV®496, EF®506, QDOT®525 (fluorescent nanocrystal probe), QDOT®545, BUV®563, QDOT®565;
iii) SUPER BRIGHT® 600 (violet laser-excitable tandem polymer dye), BV®605, eVolve 605, QDOT®585, QDOT®605;
iv) BV®650, EF®625NC, EF&700NC, Super Bright SUPER BRIGHT®, 645eVolve 655, QDOT®655;
v) QDOT®700, SUPER BRIGHT® 702;
vi) BV®711, QDOT®705;
vii) BV®750, BV®785, BV&786, QDOT®800;
viii) fluorescein isothiocyanate (FITC), AF®488, BB515, VIOBRIGHT® FITC (fluorescent dye and antibody conjugate), VIOBRIGHT® 515, Cy2, OREGON GREEN®488 (photostable fluorescent dye), DYLIGHT®488, AF®500, EF® 525NC, AF®514, AF®532;
ix) phycoerythrin (PE);
x) Cy3, AF®555, AF®546, DYLIGHT®550;
xi) PE-CF594, PE-EF610, PE-Vio615, PE/DAZZLE®594 (fluorescent label), AF®568, PE-ALEXA®594 (fluorescent dye);
xii) EF®585NC, EF®605NC, PE-TEXAS RED® (ECD) (fluorescent dye), PE-AF®610;
xiii) peridinin chlorophyll protein (PerCP), PerCP-EF®710, PERCP-Vio700, PerCPCy5.5, peridinin cyanin 5 (PE-cy5), BB660, BB700;
xiv) PEcy7, PE-Vio770, PE-AF®750, PE-AF®700, PERCP-EF®710, BB790;
xv) allophycocyanin (APC), AF®647, Cy5, EF®660, AF®660, AF®633, EF®625NC, APC-Cy5.5, EF®700NC; APC-R700;
xvi) AF®680, APC-A680, AF®700, APC-A700;
xvii) APC-hilite7 (APCH7), APC-R700, APC/Fire 750, APC-Vio 770, AF®680, APC-A750, APC-C750, AF®700, APC-EF®780, APC-cy7, Cy7, AF®750, AF®790.

A kit-of-parts as provided herein may further comprise reagents or solutions for fixing and permeabilizing cells, optionally together with instructions for use, buffer, and/or control samples. In one embodiment, the fixation reagent contains about 0.3 to 1.5% w/v, e.g. 0.5% or 1% w/v, paraformaldehyde (PFA) in phosphate buffered saline (PBS; pH=7.4). Exemplary permeabilizing reagents contain between about 0.1% and 0.5% saponin w/v diluted in PBS.

A further aspect of the invention relates to a multi-color flow cytometric method for identification and classification of a pediatric (solid) tumors, comprising the steps of:

(a) staining an aliquot of a biological sample comprising or suspected to comprise childhood tumor cells with fluorochrome-conjugated antibodies against cell surface markers as comprised in a kit-of-part according to the invention; followed by (b) contacting the stained cells with a fixation solution; followed by (c) permeabilizing the fixed and stained cells with a permeabilizing solution; followed by (d) staining the permeabilized cells with fluorochrome-conjugated antibodies against the intracellular (cytoplasmic and nuclear) markers as comprised in a kit-of-part according to the invention;

(e) analyzing the stained cells in said aliquots in a flow cytometer; and (f) storing and evaluating the data obtained.

Whereas the kits and proposed antibody combinations are exemplified herein below by the study of primary tumor tissues, it can also be applied to the analysis of bone marrow, peripheral blood, pleural effusions, ascitic fluid, pericardic effusions, cerebrospinal fluid, vitreous humor, synovial fluid, bronchoalveolar lavage, urine and any other type of biological samples obtained from pediatric patients under investigation for pediatric tumors such as non-Hodgkin lymphoma, neuroblastoma, Wilms tumor, germ cell tumors, soft tissue sarcomas (e.g. rhabdomyosarcoma, Ewing sarcoma family of tumors, chondrosarcoma, osteosarcoma) and epithelial cell tumors.

In one embodiment, the biological sample is a primary tumor tissue sample, peripheral blood, bone marrow, tissue sample such as lymph nodes, adenoid, spleen, or liver, or other type of body fluid such as cerebrospinal fluid, vitreous fluid, synovial fluid, final needle aspirate, pleural effusions or ascites, said sample being obtained from a pediatric patient.

The disclosure will now refer to the accompanying drawings and the Detailed Description that follows.

DETAILED DESCRIPTION

Figure 1:
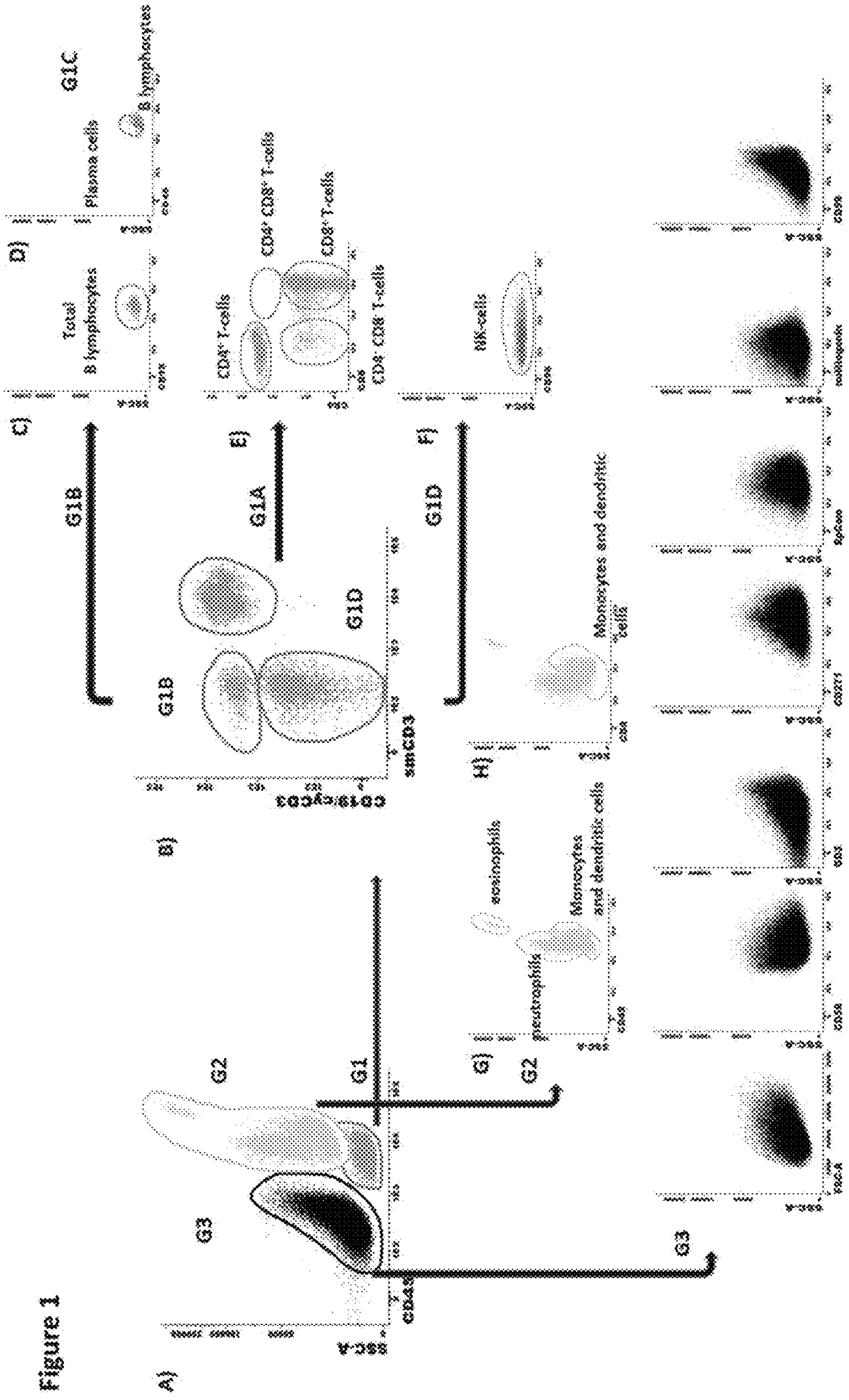
FIG. 1: Sequential gating strategy analysis to identify the major subsets populations in tumor mass sample using 2-dimensional dot plots. Panel A shows the identification of three groups of cell populations: G1 ($SSC^{lo}/CD45^{+hi}$) represents lymphocytes, G2 ($SSC^{int/hi}/CD45^{+}$) myeloid cells and G3 ($SSC^{int-hi}/CD45^{-}$) tumor cells. On G1-cells gate (Panel B), 4 additional gates allowed the identification of major lymphocyte populations: C) $CD45^{+hi}/CD19^{+}$ B-cells (G1B) and D) $CD45^{+lo}/CD19^{+}$ plasma cells (G1C); and, F) $CD45^{+}/{}_{sm}CD3^{-}/{}_{cy}CD3^{-}/CD56^{+}$ NK cells (G1D). Further T-cells ($CD45^{+hi}/{}_{sm}CD3^{+}/{}_{cy}CD3^{+}$ T-cells-G1A) where subdivided in panel E as: $CD4^{+}/CD8^{-}$, $CD4^{-}/CD8^{+}$, $CD4^{+}/CD8^{+}$ and $CD4^{-}/CD8^{-}$ T-cell subsets. On G2-cells gate (panel G), 3 additional gates based on 1 bivariate dot plot (SSC/CD45) allowed the identification of eosinophils ($SSChi/CD45^{+}$), neutrophils ($SSC^{int}/CD45^{+lo}$) and monocytes ($SSC^{int}/CD45^{+}$); further, in panel H, a bivariate dot plot (SSC/CD4) allowed a better discrimination between neutrophils/eosinophils ($SSC^{int}/CD4^{-}$) and monocytes/macrophage/dendritic cells ($SSC^{int}/CD4^{+}$) on G2-cells gate. Finally, on G3-cells gate, tumor cells were characterized as a $CD45^{-}/CD56^{+hi}/CD271^{+}/GD2^{-}/EpCAM^{-/+}/CD99^{-}/{}_{nu}Myogenin^{-}$ phenotype (Wilms tumor).

More specifically, in an example, a tissue aliquot is placed in phosphate buffered saline (PBS) and subjected to mechanical disaggregation to prepare a single-cell suspensions suitable for further flow cytometry analysis aimed at maximum cell viability and cell recovery. For this purpose, tissue is suitably placed (e.g. into a Petri dish) in PBS containing 0.5% w/v bovine serum albumin, then minced into small (2-4 mm) pieces and mechanically disaggregated with sterile needles. The resulting tumor cell suspension may be sequentially filtered (e.g. using a sterile syringe of 120 mm pore size) to eliminate cell clumps and debris, centrifuged and re-suspended in PBS/0.5 w/v % BSA, at a final concentration of $\geq 5\times10^5$ cells/tube. Aliquots of 50 µL (i.e. 50,000 cells) of the single cell suspension can then be placed in separate tubes.

As another example, e.g. in order to immunophenotype malignant cells present in metastatic sites, an ascitic fluid sample, a pleural fluid sample and/or a urine sample is collected. The sample (cell suspension) is sequentially filtered through a sterile syringe to eliminate cell clumps and debris; centrifuged and resuspended at a final concentration of $\geq 5\times10^5$ cells/tube.

Then, an aliquot of the single cell suspension is contacted with each of the fluorochrome-conjugated antibodies directed against cell surface markers comprises in a kit as defined herein above. The cells and antibody reagents are mixed well, and incubated e.g. for 30 min at RT, protected from light, to allow for antibody binding to the cell surface marker(s), if present on the cells. After this incubation, cells are washed and centrifuged to remove unbound antibodies, and approximately 50 µL of residual volume is left in each tube for further staining of intracellular (i.e. cytoplasmic and nuclear) markers according to the invention.

To that end, the cell pellet is resuspended by gentle mixing with a fixative reagent, for example Reagent A (a fixative containing PFA) of the Fix&Perm™ reagent kit (An der Grub, Vienna, Austria), followed by another incubation for 15 min at RT protected from light. Subsequently, cells are washed and the cell pellet resuspended by gentle mixing in a permeabilizing solution (for example Reagent B of the Fix&Perm™ kit containing a permeabilizing agent like saponin). After gently mixing, the appropriate volume of each of the antibodies against the intracellular markers comprised in a kit of the invention is added, mixed and incubated for 15 min at RT protected from light.

Unbound antibodies are removed by washing using for example PBS containing 0.09% $NaN_3$ and 0.5% w/v BSA, and approximately 50 µL residual volume is left in each tube. Upon mixing well, the residual volume of the cell pellet is suitably resuspended in 200 µL PBS with 0.09% $NaN_3$ and 0.5% w/v BSA and immediately measured in a multicolor flow cytometer, for example a flow cytometer equipped with 4 lasers and 13 fluorescence detectors such as a BD LSRFortessa X-20 flow cytometer equipped with 4 lasers and 13 fluorescence detectors.

For data analysis, conventional manual Boolean gating strategies or automated clustering analyses in combination or not with a direct comparison with software databases can be used via flow cytometry software programs that allow for manual and/or automatic gating and analysis of FCS files.

For example, firstly a gate (G1) on SSClo/FSClo/CD45hi cells is performed for the identification of lymphocytes. This G1-cell population may then be further subsetted by drawing 4 additional gates for the identification of lymphocyte subsets in the following manner: CD45$^{hi}$/smCD3$^+$/cyCD3$^+$ for T cells (G1A), CD45$^{hi}$/CD19$^+$ for B cells (G1B), CD45$^{+lo}$/CD19$^+$ for plasma cells (G1C) and CD45$^-$/smCD3$^-$/cyCD3$^-$/CD56$^+$ for NK cells (G1D). T-cells can be further subdivided into CD4$^+$/CD8$^-$, CD4$^-$/CD8$^+$, CD4$^+$/CD8$^+$ and CD4$^-$/CD8$^-$ T-cell subsets.

A second gate (G2) to include SSC$^{int/hi}$/FSC$^{int/hi}$/CD45$^+$ cells can be drawn for the identification of myeloid cells. Further subsets of myeloid cell populations may be achieved by establishing a gate on CD45$^-$/CD4$^+$ myeloid cells to identify monocytes and dendritic cells vs neutrophils and eosinophils (SSC$^{hi}$/CD45$^+$).

Finally, a gate (G3) can be performed on CD45$^-$ cells to select tumor cells, erythroblasts, endothelial and mesenchymal stromal cells, where Wilms tumor cells (FIG. 1) are characterized by a CD45$^-$/CD56$^{+hi}$/CD271$^+$/GD2$^-$/EpCAM$^{-/+}$/CD99$^-$/$_{nu}$Myogenin$^-$ phenotype (FIG. 1), rhabdomyosarcoma cells by a CD45$^-$/CD56$^{+hi}$/CD271$^{+hi}$/GD2$^-$/EpCAM$^-$/CD99$^-$/$_{nu}$Myogenin$^+$ profile (FIG. 2), neuroblastoma cells CD45$^-$/CD56$^{+hi}$/CD271$^{-/+}$/GD2$^{+hi}$/EpCAM$^-$/CD99$^-$/$_{nu}$Myogenin$^-$ (FIG. 3) and PNET cells CD45$^-$/CD56$^+$/CD271$^{+hi}$/GD2$^{+lo}$/EpCAM$^-$/CD99$^+$/$_{nu}$Myogenin$^-$. FIG. 1 illustrates all exemplary data analysis steps in a Wilms tumor sample. Table 2 shows the percentage of neoplastic cells and immune cells in the different pediatric solid tumor samples analysed.

As will be appreciated by a person skilled in the art, an antibody panel, kit or kit according to the invention is advantageously used in the field of pediatric cancer diagnosis; for example in early diagnosis, diagnostic subclassification, staging and/or monitoring of pediatric cancer both at the primary tumor tissue site and at metastatic sites (e.g. ascitic fluid, pleural effusions, urine, bone marrow, cerebrospinal fluid, lymph node and bronchoalveolar lavage, among other tumor specimens) and peripheral blood. It allows both to accurately distinguish between the tumor cells and other residual cells in the sample, and to characterize the distinct subsets of immune cells coexisting with the tumor cells in the same sample. In addition, it provides tools for fast classification of pediatric solid tumors with high sensitivity (detection of $10^{-1}$ to $10^{-5}$ tumor cells among other cells in the sample) and it further provides numerical and phenotypic information about the tumor-associated microenvironment, as it allows identification and enumeration of the major lymphocyte, neutrophil, monocyte/macrophage and dendritic cell populations and mesenchymal cells, in the infiltrated or non-infiltrated patient specimens.

The procedure includes the following sequential steps: i) to obtain a biological sample from a patient suspected of suffering from a pediatric cancer; ii) to stain such biological sample with a panel of ≥12-antibodies (e.g. a combination according to Table 1) conjugated with 8-distinct fluorochromes in 8-color antibody stainings, aimed at the identification and classification of the tumor cells as well as of the infiltrating immune cells coexisting in the sample; iii) to measure the stained cells in a conventional >8-color flow cytometry instrument, and; iv) to analyze the flow cytometric data obtained using dedicated software tools in order to distinctly identify tumor cells vs normal cells coexisting in the sample, further enumerate such tumor cells, define the levels of expression per cell of each marker being expressed on it, classify the tumor cells into distinct WHO diagnostic entities according to their immunophenotypic profile, and, identify and enumerate the distinct populations of immune cells and their major subsets that coexist with the tumor cells in the sample.

The procedure here described can be used for the diagnosis and classification of the most common types of pediatric tumors including: i) neuroectodermal neoplasias, such as neuroblastoma, ganglioneuroblastoma, ganglioneuroma, extraosseous Ewing sarcoma and classical Ewing sarcoma for which most useful antigens are CD45$^-$, CD56$^{++}$, CD99$^{-or+}$, GD2$^{++}$ and CD271$^+$; ii) tumors with myofibroblastic cell differentiation as assessed by a CD45$^-$, CD56$^+$, anti-$_{nu}$Myogenin$^+$, anti-$_{nu}$MyoD1$^+$ and CD271$^+$ phenotype; iii) identification of commitment into multiple cell lineages as defined by the expression pattern of e.g. CD45$^-$, CD56$^{++}$, CD271$^+$ and EpCAM$^+$ in Wilms tumor; and iv) T and B-lymphoblastic lymphoma/leukemia which characteristically show expression of $cyCD3^{+}$ and $CD45^{++}CD19^{-}$, vs $CD19^{+}$ $CD45^{-/+}$ $cyCD3^{-}$ tumor cells.

Furthermore, the invention also permits simultaneous flow cytometric identification of lymphocytes ($CD45^{++}$/$SSC^{lo}$ cells) including $cyCD3^{+}/CD3^{+}$ T-cells, $CD19^{+}$ B-cells and $CD19^{-}/CD3^{-}/CD56^{+}$ NK cells, $CD19^{+}/CD45^{lo}$ plasma cells and $CD4^{+}/SSC^{int}$ monocytes and dendritic cells, plus CD271++ mesenchymal cells and endothelial cells.

Based on the expression of CD56, CD4 and CD8, T-cells can be further divided into $CD4^{+}/CD8^{-}$, $CD4^{-}/CD8^{+}$, $CD4^{+}/CD8^{+}$, $CD4^{-}/CD8^{-}$ T cells; each of these T-cell subsets can be further divided into subsets that express or not CD56. Simultaneously, $CD56^{+}$ NK cells can be further subdivided into $CD56^{+hi}$, $CD56^{+lo}/CD8^{-}$, $CD56^{+lo}/CD8^{+}$ NK subsets.

Notably, each of the kits and antibody combinations provided herein to identify and classify the tumor cell population, also provide means to quantify protein expression levels per tumor cell; therefore, it provides critical information, not only for the diagnosis, classification and monitoring of pediatric solid tumors, but also for selecting appropriate targeted therapies (e.g. anti-GD2 in $GD2^{+}$ neuroblastoma and other $GD2^{+}$ tumors).

The invention might also be used to detect and count tumor cells in bone marrow and peripheral blood samples prior to autologous stem cell transplantation, or for monitoring purposes after any type of therapy had been given to the patient. Furthermore, this invention can also be used to identify neoplastic and non-neoplastic cells in small and/or paucicellular samples such as vitreous fluid, cerebrospinal fluid and fine needle aspirated tissue samples for staging purposes, diagnosis of disease recurrence or patient monitoring at residual disease levels.

The diagnostic outcome of a flow cytometric method of the invention is advantageously used to aid in selecting an appropriate (targeted) therapy such as anti-GD2 antibody-based or chimeric antigen receptor (CAR) T-cell therapy.

The invention also provides the use of a kit-of-parts as herein disclosed in the diagnosis and classification of one or more pediatric tumors. For example, the pediatric tumor is selected from: i) neuroectodermal neoplasias, such as neuroblastoma, ganglioneuroblastoma, ganglioneuroma, extraosseous Ewing sarcoma and classical Ewing sarcoma; ii) tumors with myofibroblastic cell differentiation; iii) identification of commitment into multiple cell lineages; and iv) T and B-lymphoblastic lymphoma/leukemia.

The invention is exemplified by the examples below, which are provided for illustrating purposes and in no manner limit the scope.

EXAMPLE 1

Analysis of a Tumor Mass Sample

Sample collection. Solid tumor specimens were collected at the surgical room from fifty-five pediatric patients; tumor samples were sent to pathology and they were divided into two aliquots by an experienced pathologist: one was used for conventional pathology and the second for flow cytometry. The tissue aliquot used for flow cytometry was immediately placed in phosphate buffered saline (PBS) in wet ice and transported to the flow cytometry laboratory. Once the specimen arrived it was weighted, a physical description was recorded, and the sample was further divided into two small fragments: one for fresh-frozen storage at −80° C. and the other for immediate mechanical disaggregation.

Mechanical disaggregation of the tumor specimen. Fifty-five tumor tissue specimens were immediately disaggregated into single-cell suspensions suitable for further flow cytometry analysis aimed at maximum cell viability and cell recovery. For this purpose, the tissue was placed into a Petri dish in 2 ml PBS containing 0.5% bovine serum albumin (BSA; Calbiochem, La Jolla, CA). The tumor specimen was then minced into small pieces (2-4 mm) with a scalpel blade and mechanically disaggregated with sterile needles. Afterward, the tumor cell suspension was sequentially filtered through a sterile Filcon syringe (120 mm pore size) to eliminate cell clumps and debris, centrifuged (10 min at 540 g) and re-suspended in 500 μl of PBS containing 0.5% BSA, at a final concentration of ≥5×105 cells/tube. Aliquots of 50 μL (i.e. 50,000 cells) of the single cell suspension were then placed in a different tube. A total of 4 distinct aliquots/per sample were stained per tube to be acquired.

Staining of the sample. Fifty μl of sample (single cell suspension of the disaggregated tissues) was added to each of the 4 tube aliquots, followed by adding the appropriate volumes (saturating concentrations) of each of the corresponding reagent compositions, comprising antibodies directed against cell surface markers, as recommended for this single tube panels i) CyCD3 BV®421+CD271 BV®421/CD45 BV®510 CD99 FITC+CD8 FITC/nuMyogenin PE/EpCAM PERCPcy5.5+CD4 PERCPcy5.5/CD56 PEcy7/GD2 AF®647/csmD3 APC-H7+CD19 APC-H7 (i.e. antibody combination 1 in Table 1);

ii) CyCD3 BV®421+CD271 BV®421/CD45 PO/CD99 FITC+CD8 FITC/nuMyoD1 PE/EpCAM PERCPcy5.5+CD4 PERCPcy5.5/CD56 PEcy7/GD2 AF®647/cyCD3 APC-H7+CD19 APC-H7 (antibody combination 2 in Table 1);

iii) CyCD3 BV®786+CD271 BV®786/HLADR APC/CD45 AF®700/CD30 APCH7/CD71 BV®650/CD95 BV®421/CD99 FITC+CD8 FITC/nuMyoD PE/CD40 BV®711/EpCAM PERCPcy5.5+CD4 PERCPcy5.5/CD56 PEcy7/GD2 BV®510/smCD3 APC-H7+CD19 APC-H7 (antibody combination 17 in Table 1)

iv) CyCD3 BV®786+CD271 BV®786/HLADR PECF594/CD45 AF®700/CD30 BV®650/CD99 FITC+CD8 FITC/GD2 BV®510/osteopontin APC/numyogenin PE/CD40 BV®711/EpCAM PERCPcy5.5+CD4 PERCPcy5.5/CD56 PEcy7/OCT3 APCH7/CD95 BV®421/smCD3 BV®605+CD19 BV®605 (antibody combination 18 in Table 1).

Subsequently, the cells and antibody reagents were mixed well, and they were incubated for 30 min at RT protected from light. After this incubation, 2 mL of PBS with 0.09% NaN3 and 0.5% BSA was added to the cell pellet, mixed well and centrifuged for 5 min at 540×g. Then, the supernatant was discarded using a Pasteur pipette or vacuum system without disturbing the cell pellet, and approximately 50 μL of residual volume was left in each tube. The cell pellet was resuspended by gentle mixing and 100 μL of Reagent A (fixative containing PFA) of the Fix&Perm™ reagent kit (An der Grub, Vienna, Austria) was added, followed by another incubation for 15 min at RT protected from light. Subsequently, 2 mL of PBS with 0.09% $NaN_3$ containing 0.5% BSA was added to the cell pellet, mixed well and centrifuged for 5 min at 540 g.

Then, the supernatant was discarded using a Pasteur pipette or vacuum system without disturbing the cell pellet, and approximately 50 μL of residual volume was left in each tube; the cell pellet was resuspended by gently mixing and 100 μL of Reagent B (permeabilizing solution containing saponin) of the Fix&Perm™ kit was added. After gently mixing, the appropriate volume of each of the antibodies against intracellular markers (nuMyoD1, nuMyogenin, OCT3 and cyCD3) was added, mixed and incubated for 15 min at RT protected from light. Afterward, 2 mL of PBS containing 0.09% $NaN_3$ and 0.5% BSA was added to the cell pellet, mixed well and centrifuged for 5 min at 540 g, the supernatant was discarded using a Pasteur pipette or vacuum system without disturbing the cell pellet, and approximately 50 μL residual volume was left in each tube. Upon mixing well, the residual volume the cell pellet was resuspended in 200 μL PBS with 0.09% NaN3 and 0.5% BSA and immediately measured in a BD LSRFortessa X-20 flow cytometer equipped with 4 lasers and 13 fluorescence detectors.

Data analysis. Firstly, a gate (G1) on SSC$^{lo}$/FSC$^{lo}$/CD45$^{hi}$ cells was performed for the identification of lymphocytes; and selected then, this G1-cells were further subsetted by drawing 4 additional gates for the identification of lymphocyte subsets as follows: CD45$^{hi}$/smCD3$^{+}$/cyCD3$^{+}$ for T cells (G1A), CD45$^{hi}$/CD19$^{+}$ for B cells (G1B), CD45$^{+lo}$/CD19$^{+}$ for plasma cells (G1C) and CD45$^{+}$/smCD3$^{-}$/cyCD3$^{-}$/CD56$^{+}$ for NK cells (G1D). T-cells were further subdivided into CD4$^{+}$/CD8$^{-}$, CD4$^{-}$/CD8$^{+}$, CD4$^{+}$/CD8$^{+}$ and CD4$^{-}$/CD8$^{-}$ T-cell subsets (panel E in FIG. 1). A Second gate (G2) to include SSC$^{int/hi}$/FSC$^{int/hi}$/CD45$^{+}$ cells was drawn for the identification of myeloid cells. Further subsets of myeloid cell populations was achieved by establishing a gate on CD45$^{+}$/CD4$^{+}$ myeloid cells to identify monocytes and dendritic cells vs neutrophils and eosinophils (SSC$^{hi}$/CD45$^{+}$). Finally, a gate (G3) was performed on CD45$^{-}$ cells to select tumor cells, erythroblasts, endothelial and mesenchymal stromal cells, where Wilms tumor cells (FIG. 1) are characterized by a CD45$^{-}$/CD56$^{+hi}$/CD271$^{+}$/GD2$^{-}$/EpCAM$^{-+}$/CD99$^{-}$/$_{nu}$Myogenin$^{-}$ phenotype (FIG. 1), rhabdomyosarcoma cells by a CD45$^{-}$/CD56$^{+hi}$/CD271$^{+hi}$/GD2$^{-}$/EpCAM$^{-}$/CD99$^{-}$/$_{nu}$Myogenin$^{+}$ profile (FIG. 2), neuroblastoma cells CD45$^{-}$/CD56$^{+hi}$/CD271$^{-/+}$/GD2$^{+hi}$/EpCAM$^{-}$/CD99$^{-}$/$_{nu}$Myogenin$^{-}$ (FIG. 3) and PNET cells CD45$^{-}$/CD56$^{+}$/CD271$^{+hi}$/GD2$^{+lo}$/EpCAM$^{-}$/CD99$^{+}$/$_{nu}$Myogenin. FIG. 1 illustrates all data analysis steps in a Wilms tumor sample and table 2 shows the percentage of neoplastic cells and immune cells in the different pediatric solid tumor samples analysed.

EXAMPLE 2

Analysis of Ascitic Fluid, Pleural Fluid and Urine Sample

Sample collection. In order to immunophenotype malignant cells present in metastatic sites, samples from 5 children previously diagnosed with pediatric cancer were studied: 1 ascitic fluid, 3 pleural fluid and 1 urine sample. Samples were collected at the surgical room or at the intensive care unit and processed either at diagnosis or at relapse, by following the sequential steps described below. Firstly, the sample (cell suspension) was sequentially filtered through a sterile Filcon syringe (120 mm pore size) to eliminate cell clumps and debris; then, it was centrifuged (10 min at 540 g) and resuspended in 500 μl of PBS containing 0.5% BSA, at a final concentration of >5×105 cells/tube. Four aliquots of 50 μL (i.e. 50,000 cells) of the single cell suspension were then made and placed in different tubes.

Staining of the sample. One hundred μl of the above processed cell suspensions were added to each of the 4 tube aliquots prepared per sample, followed by the appropriate volumes (saturating concentrations) of each of the corresponding antibodies directed against cell surface markers, as recommended for the following single tube fluorochrome-conjugated antibody combinations: i) CyCD3 BV®421+CD271 BV®421/CD45 BV®510/CD99 FITC+CD8 FITC/nuMyogenin PE+nuMyoD1 PE/EpCAM PERCPcy5.5+CD4 PERCPcy5.5/CD56 PEcy7/GD2 APC/smCD3 APC-H7+CD19 APC-H7 (i.e. antibody combination 3 in Table 1); ii) CyCD3 BV®421+CD271 BV®421/CD45 AF®700/CD99 FITC+CD8 FITC/GD2 BV®510/osteopontin APC+BAP APC/nuMyogenin PE/EpCAM PERCPcy5.5+CD4 PERCPcy5.5/CD56 PEcy7/OCT-3/4/APCH7+PLAP APCH7/smCD3 BV®786+CD19 BV®786 (i.e. antibody combination 7 in Table 1) iii) CyCD3 BV®421+CD271 BV®421/HLADR APC/CD45 AF®700/CD30 APCH7/GD2 BV®510/CD99 FITC+CD8 FITC/nuMyogenin PE/CD40 BV®711/EpCAM PERCPcy5.5+CD4 PERCPcy5.5/CD56 PEcy7/smCD3 APC-H7+CD19 APC-H7 (i.e. antibody combination 13 in Table 1) and iv) CyCD3 BV®786+CD271 BV®786/CD45 AF®700/PLAP APCH7/CD99 FITC+CD8 FITC/GD2 BV®510/osteopontin APC+BAP APC/nuMyogenin PE/CD95 BV®421/CD30 BV®650/CD40 BV®711//EpCAM PERCPcy5.5+CD4 PERCPcy5.5/HLADR PECF594/CD56 PEcy7/smCD3 BV®605+CD19 BV®605 (i.e. antibody combination 24 in Table 1). After the cells and antibody reagents directed against cell surface markers were mixed well, they were incubated for 30 min at RT protected from light. After this incubation, 2 mL of PBS containing 0.09% NaN3 and 0.5% BSA was added to the cell pellet, mixed well and centrifuged for 5 min at 540 g. Then, the supernatant was discarded using a Pasteur pipette or vacuum system without disturbing the cell pellet, and approximately 50 μL of residual volume was left in each tube. The cell pellet was resuspended by gentle mixing and 100 μL of Reagent A (fixative containing PFA) of the Fix&Perm™ reagent kit (An der Grub, Vienna, Austria) was added, followed by another incubation for 15 min at RT protected from light. Subsequently, 2 mL of PBS with 0.09% NaN3 and 0.5% BSA was added to the cell pellet, mixed well and centrifuged for 5 min at 540 g. Then, the supernatant was discarded using a Pasteur pipette or vacuum system without disturbing the cell pellet, and approximately 50 μL of residual volume was left in each tube; the cell pellet was resuspended by gently mixing and 100 μL of Reagent B (permeabilizing solution containing saponin) of the Fix&Perm™ kit was added. After gently mixing, the appropriate volume of each of the intracellular antibodies (nuMyoD1, nuMyogenin, Osteopontin, BAP, PLAP and cyCD3 APC-H7) was added, mixed and incubated for 15 min at RT protected from light. Afterward, 2 mL of PBS with 0.09% NaN3 and 0.5% BSA was added to the cell pellet, mixed well and centrifuged for 5 min at 540 g, the supernatant was discarded using a Pasteur pipette or vacuum system without disturbing the cell pellet, and approximately 50 μL residual volume was left in each tube. Upon mixing well, the residual volume, the cell pellet was resuspended in 200 μL PBS containing 0.09% NaN3 and 0.5% BSA and immediately measured in a BD Symphony X-20 flow cytometer equipped with 5 lasers and 48 fluorescence detectors.

Data analysis. Firstly, a gate (G1) on SSC$^{lo}$/FSC$^{lo}$/CD45$^{+hi}$ cells was performed for the identification of lymphocytes and selected; then, this G1-cells were further subseted by drawing 4 additional gates for the identification of lymphocyte subsets as follows: CD45$^{+hi}$/smCD3$^{+}$/cyCD3$^{+}$ for T cells (G1A), CD45$^{+hi}$/CD19$^{+}$ for B cells (G1B), CD45$^{+lo}$/CD19$^{+}$ for plasma cells (G1C) and CD45$^{+}$/smCD3$^{-}$/cyCD3$^{-}$/CD56$^{+}$ for NK cells (G1D). T-cells were further subdivided into CD4$^{+}$/CD8$^{-}$, CD4$^{-}$/CD8$^{+}$, CD4$^{+}$/CD8$^{+}$ and CD4$^{-}$/CD8$^{-}$ T-cell subsets (panel E in FIG. 2).

Figure 2:
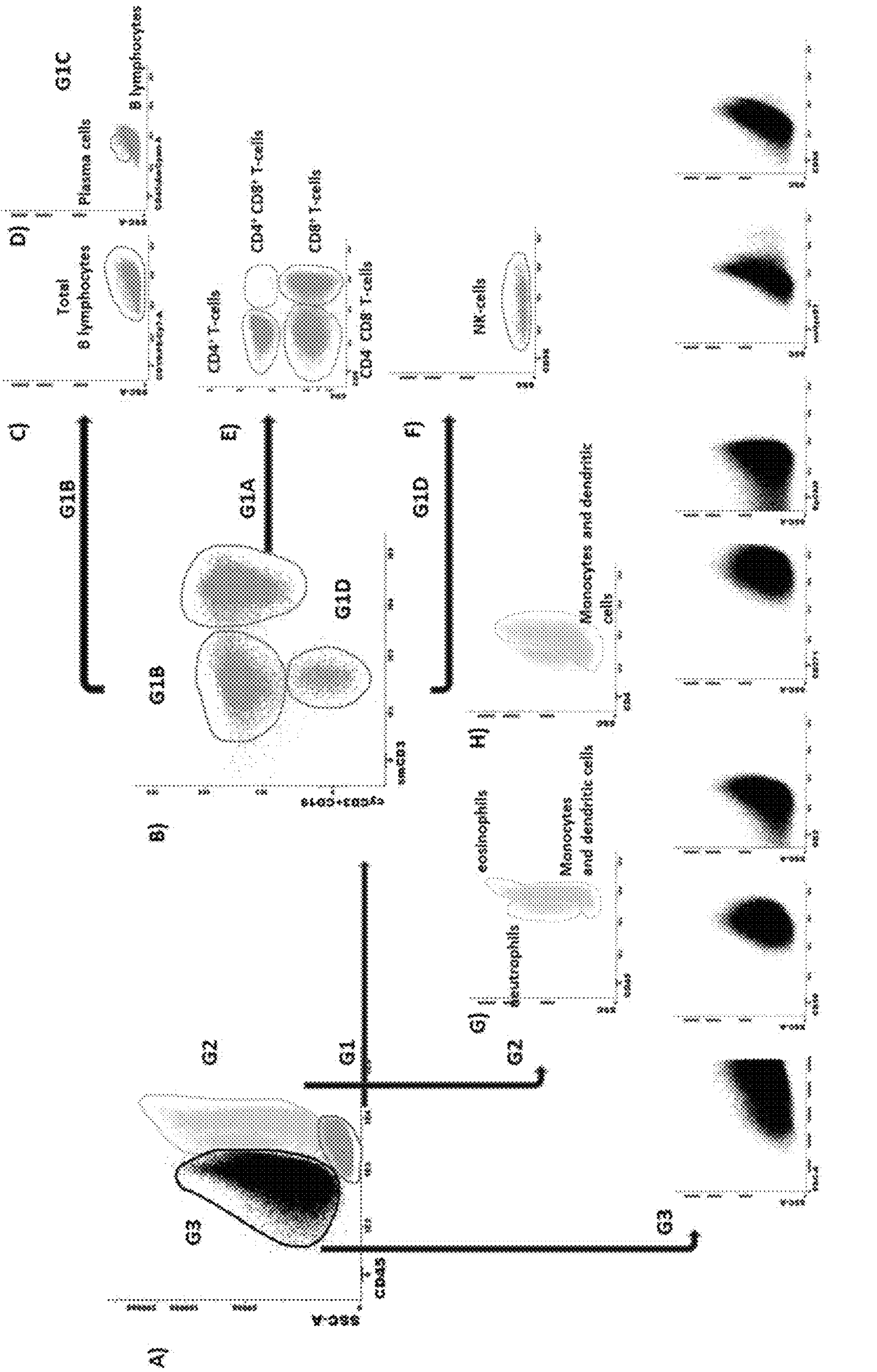
FIG. 2: Sequential gating strategy to identify the major subsets populations in pleural effusion sample using 2-dimensional dot plots. Panel A shows the identification of three groups of cell populations: G1 ($SSC^{lo}/CD45^{+hi}$) represents lymphocytes, G2 ($SSC^{int/hi}/CD45^{+}$) myeloid cells and G3 ($SSC^{hi}/CD45^{-}$) tumor cells. On G1-cells (Panel B), 4 additional gates allowed the identification of major lymphocyte populations: C) $CD45^{+hi}/CD19^{+}$ B-cells (G1B) and $CD45^{+lo}/CD19^{+}$ plasma cells (G1C); and, D) $CD45^{+}/{}_{sm}CD3^{-}/{}_{cy}CD3^{-}/CD56^{+}$ NK cells (G1D). Further T-cells ($CD45^{+hi}/{}_{sm}CD3^{+}/{}_{cy}CD3^{+}$ T-cells-G1A) where subdivided in panel E) $CD4^{+}/CD8^{-}$, $CD4^{-}/CD8^{+}$, $CD4^{+}/CD8^{+}$ and $CD4^{-}/CD8^{-}$ T-cell subsets. G) After selection of G2-cells, 3 additional gates based on 1 bivariate dot plot (SSC/CD45) allowed the identification of eosinophils ($SSChi/CD45^{+}$), neutrophils ($SSC^{int}/CD45^{+lo}$) and monocytes ($SSC^{int}/CD45^{+}$); H) further bivariate dot plot (SSC/CD4) analysis of G2 population allowed better discrimination between neutrophils ($SSC^{int}/CD4^{-}$) and monocytes/dendritic cells ($SSC^{int}/CD4^{+}$). Finally, the selected G3 population was analyzed for selection and identification of most relevant cell markers to classify tumor cells being characterized by a $CD45^{-}/CD56^{+hi}/CD271^{+hi}/GD2^{-}/EpCAM^{-}/CD99^{-}/{}_{nu}MyoD1^{+}$ phenotype (Rhabdomyosarcoma).

Secondly, a gate (G2) to include $SSC^{int/hi}$/$FSC^{int/hi}$/$CD45^{+}$ cells was done to identify myeloid cells. Further subsets of myeloid cell populations was achieved by establishing a gate on $CD45^{+}$/$CD4^{+}$ myeloid cells to identify monocytes and dendritic cells vs. neutrophils and eosinophils. Finally, a gate (G3) was performed on $CD45^{-}$ cells to select the tumor cells, Wilms tumor cells showing a $CD45^{-}$/$CD56^{+}$/$CD271^{+}$/$GD2^{-}$/$EpCAM^{-/+}$/$CD99^{-}$/$_{nu}$Myogenin$^{-}$ phenotype, rhabdomyosarcoma cells being $CD45^{-}$/$CD56^{+}$/$CD271^{+}$/$GD2^{-}$/$EpCAM^{-}$/$CD99^{-}$/$_{nu}$Myogenin$^{+}$ (FIG. 2), neuroblastoma cells by $CD45^{-}$/$CD56^{+}$/$CD271^{-}$/$GD2^{+hi}$/$EpCAM^{-}$/$CD99^{-}$/$_{nu}$Myogenin$^{-}$, and PNET cells by $CD45^{-}$/$CD56^{+}$/$CD271^{+hi}$/$GD2^{+lo}$/$EpCAM^{-}$/$CD99^{+}$/$_{nu}$Myogenin$^{-}$. FIG. 2 illustrates all gating steps performed during data analysis for the identification in a pleural fluid sample infiltrated by Rhabdomyosarcoma cells both the tumor cell and residual normal reactive immune cells; in turn, Table 3 shows the percentage of neoplastic cells identified in the five body fluid samples analyzed.

EXAMPLE 3

Analysis of a Bone Marrow Sample

Sample collection. Twenty-three bone marrow and ten peripheral blood samples collected from 23 cancer patients were investigated for the presence of metastatic dissemination during staging procedures. At least $10\times10^{6}$ nucleated cells from each sample were stained in 4 distinct tubes/aliquots per peripheral blood and bone marrow sample using the EUROFLOW bulk lysis protocol, as previously described (Flores-Montero et al., Leukemia. 2017 October; 31(10):2094-2103) for acquisition of $>5\times10^{6}$ cells/tube. Briefly, 2 ml of each sample plus 50 mL of ammonium chloride lysing solution were mixed in a 50 ml Falcon tube and incubated for 15 min in a roller or a sample-shaker device. Afterward, the sample was centrifuged at 800 g for 10 min and the supernatant discarded using a Pasteur pipette without disturbing the cell pellet. Upon discarding the supernatant, the tube was refilled with PBS containing 0.09% $NaN_3$ and 0.5% BSA to a final volume of 50 ml and centrifuged once again at 800 g (5 min). Without disturbing the cell pellet, the supernatant was discarded, and the cell pellet was resuspended in 2 mL of PBS with 0.09% $NaN_3$ and 0.5% BSA. Then, the cells were transferred to a 5 mL polystyrene round-bottom Falcon tube ("FACS tube") in a volume of 300 µl/tube. Such volume was completed with PBS containing 0.09% $NaN_3$ and 0.5% BSA to reach 2 ml (final volume), gently mixed and centrifuged at 540 g for 5 min; then, the supernatant was removed using a Pasteur pipette without disturbing the cell pellet. This procedure was repeated twice. The final cell concentration was adjusted with PBS with 0.09% $NaN_3$ and 0.5% BSA to 5×105 cells/µL and around 100 µL (i.e. 10 million cells) of the final cell suspension/sample were used per tube to be stained and measured in the flow cytometer.

Staining of the sample. One hundred µl of the above processed cell suspensions were added to each of the 4 tube aliquots prepared per sample, followed by the appropriate volumes (saturating concentrations) of each of the corresponding antibodies directed against cell surface markers, as recommended for the following single tube fluorochrome-conjugated antibody combinations: i) CyCD3 BV421+CD271 BV421/CD45 BV510/CD99 FITC+CD8 FITC/nuMyogenin PE+nuMyoD1 PE/EpCAM PERCPcy5.5+CD4 PERCPcy5.5/CD56 PEcy7/GD2 APC/smCD3 APC-H7+CD19 APC-H7 (i.e. antibody combination 3 in Table 1); ii) CyCD3 BV421+CD271 BV421/CD45 AF700/CD99 FITC+CD8 FITC/GD2 BV510/osteopontin APC+BAP APC/nuMyogenin PE/EpCAM PERCPcy5.5+CD4 PERCPcy5.5/CD56 PEcy7/OCT-3/4/APCH7+PLAP APCH7/smCD3 BV786+CD19 BV786 (i.e. antibody combination 7 in Table 1) iii) CyCD3 BV421+CD271 BV421/HLADR APC/CD45 AF700/CD30 APCH7/GD2 BV510/CD99 FITC+CD8 FITC/nuMyogenin PE/CD40 BV711/EpCAM PERCPcy5.5+CD4 PERCPcy5.5/CD56 PEcy7/smCD3 APC-H7+CD19 APC-H7 (i.e. antibody combination 13 in Table 1) and iv) CyCD3 BV786+CD271 BV786/CD45 AF700/PLAP APCH7/CD99 FITC+CD8 FITC/GD2 BV510/osteopontin APC+BAP APC/nuMyogenin PE/CD95 BV421/CD30 BV650/CD40 BV711/ /EpCAM PERCPcy5.5+CD4 PERCPcy5.5/HLADR PECF594/CD56 PEcy7/smCD3 BV605+CD19 BV605 (i.e. antibody combination 24 in Table 1). After the cells and antibody reagents directed against cell surface markers were mixed well, they were incubated for 30 min at RT protected from light. After this incubation, 2 mL of PBS containing 0.09% NaN3 and 0.5% BSA was added to the cell pellet, mixed well and centrifuged for 5 min at 540 g. Then, the supernatant was discarded using a Pasteur pipette or vacuum system without disturbing the cell pellet, and approximately 50 µL of residual volume was left in each tube.

The cell pellet was resuspended by gentle mixing, and 100 µL of Reagent A (fixative containing PFA) of the Fix&Perm™ reagent kit (An der Grub, Vienna, Austria) was subsequently added, followed by another incubation for 15 min at RT protected from light. Subsequently, 2 mL of PBS with 0.09% NaN3 and 0.5% BSA was added to the cell pellet, mix well and centrifuged for 5 min at 540 g. Then, the supernatant was discarded using a Pasteur pipette or vacuum system without disturbing the cell pellet, and approximately 50 µL of residual volume was left in each tube; the cell pellet was resuspended by gently mixing and 100 µL of Reagent B (permeabilizing solution containing saponin) of the Fix&Perm™ kit was subsequently added. After gently mixing, the appropriate volume of each of the intracellular antibodies (nuMyoD1, nuMyogenin PE, Osteopontin, BAP, OCT-3/4, PLAP and cyCD3) was added, mixed and incubated for 15 min at RT protected from light. Afterward, 2 mL of PBS with 0.09% NaN3 and 0.5% BSA was added to the cell pellet, mixed well and centrifuged for 5 min at 540 g, the supernatant was discarded using a Pasteur pipette or vacuum system without disturbing the cell pellet, and approximately 50 µL residual volume was left in each tube. Upon mixing well the residual volume, the cell pellet was resuspended in 200 µL PBS with 0.09% NaN3 and 0.5% BSA, and immediately measured in a BD LSRFortessa X-20 flow cytometer equipped with 4 lasers and 13 fluorescence detectors.

Figure 3:
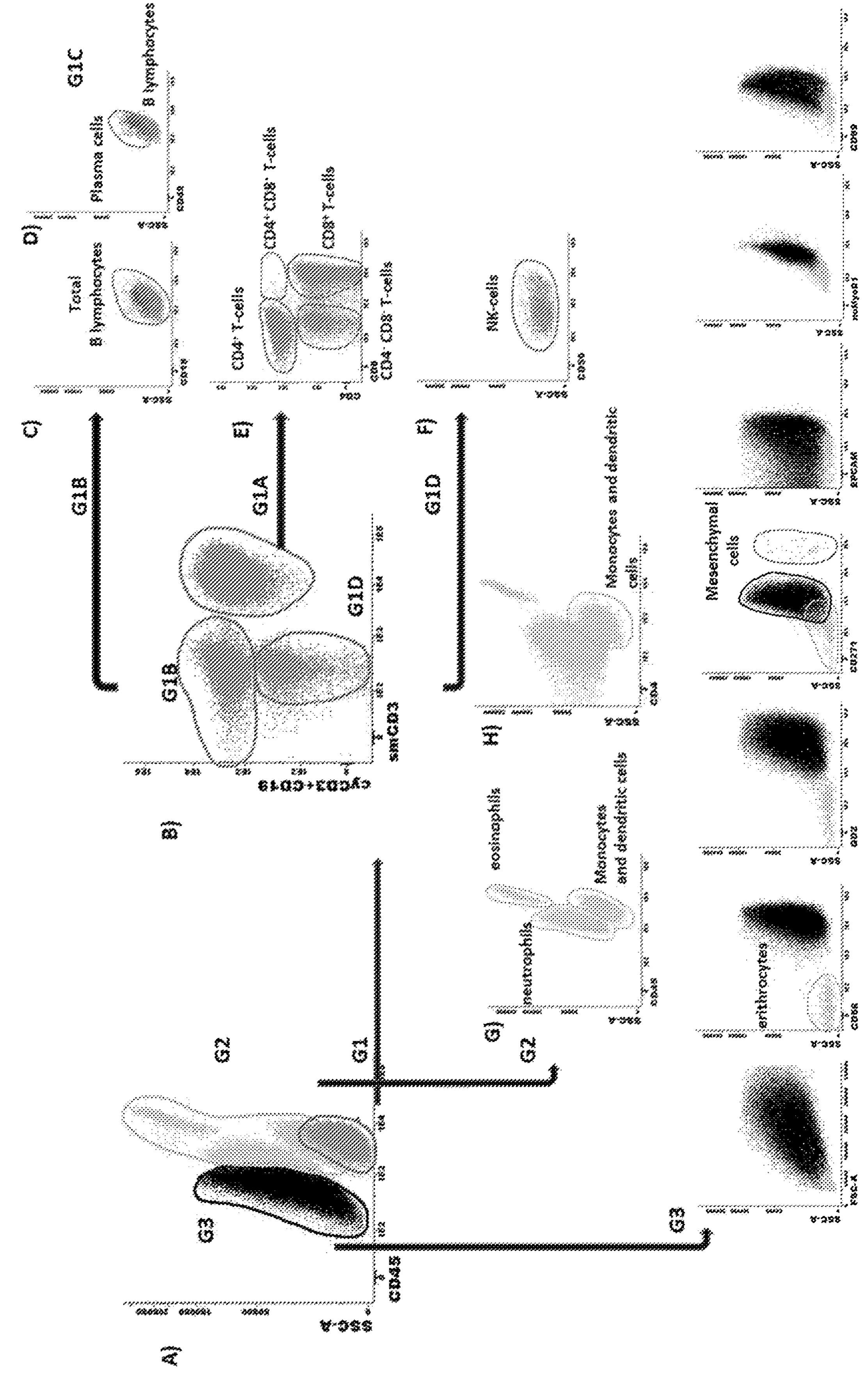
FIG. 3: Sequential gating strategy to identify the major subsets populations in bone marrow using 2-dimensional dot plots. Panel A shows the identification of three groups of cell populations G1 ($SSC^{lo}/CD45^{+hi}$) represents lymphocytes, G2 ($SSC^{int/hi}/CD45^{+}$) myeloid cells and G3 ($SSC^{hi}/CD45^{-}$) tumor cells. On G1 cells gate (Panel B), 4 additional gates allowed the identification of major lymphocyte populations: C) $CD45^{+hi}/CD19^{+}$ B-cells (G1B) and $CD45^{+lo}/CD19^{+}$ plasma cells (G1C); and, D) $CD45^{+}/{}_{sm}CD3^{-}/{}_{cy}CD3^{-}/CD56^{+}$ NK cells (G1D). Further T-cells ($CD45^{+hi}/{}_{sm}CD3^{+}/{}_{cy}CD3^{+}$ T-cells-G1A) where subdivided in panel E) $CD4^{+}/CD8^{-}$, $CD4^{-}/CD8^{+}$, $CD4^{+}/CD8^{+}$ and $CD4^{-}/CD8^{-}$ T-cell subsets. G) After selection of G2-cells, 3 additional gates based on 1 bivariate dot plot (SSC/CD45) allowed the identification of eosinophils ($SSChi/CD45^{+}$), neutrophils ($SSC^{int}/CD45^{+lo}$) and monocytes ($SSC^{int}/CD45^{+}$); H) further bivariate dot plot (SSC/CD4) analysis of G2 population allowed better discrimination between neutrophils ($SSC^{int}/CD4^{-}$) and monocytes/dendritic cells ($SSC^{int}/CD4^{+}$). Finally, on G3-cells gate, tumor cells were characterized by a $CD45^{-}/CD56^{+hi}/CD271^{-/+}/GD2^{++}/EpCAM^{-}/CD99^{-}/{}_{nu}MyoD1$ phenotype (Neuroblastoma), while nucleated erythroid cells presented as $SSC^{lo}/CD45^{-}/CD56^{-}$ and mesenchymal cells as $SSC^{hi}/CD45^{-}/CD56^{-/+lo}/CD271^{+hi}$.

Data analysis. Firstly, a gate (G1) on $SSC^{lo}$/$FSC^{lo}$/$CD45^{+}$ $_{hi}$ cells was performed for the identification of lymphocytes and selected; then, this G1-cells were further subsetted by drawing 4 additional gates for the identification of lymphocyte subsets as follows: $CD45^{+hi}$/$smCD3^{+}$/$cyCD3^{+}$ for T cells (G1A), $CD45^{+hi}$/$CD19^{+}$ for B cells (G1B), $CD45^{+lo}$/$CD19^{+}$ for plasma cells (G1C) and $CD45^{+}$/$smCD3^{-}$/$cyCD3^{-}$/$CD56^{+}$ for NK cells (G1D). T-cells were further subdivided into $CD4^{+}$/$CD8^{-}$, $CD4^{-}$/$CD8^{+}$, $CD4^{+}$/$CD8^{+}$ and $CD4^{-}$/$CD8^{-}$ T-cell subsets (panel E in FIG. 3). A Second gate (G2) to include $SSC^{int/hi}$/$FSC^{int/hi}$/$CD45^{+}$ cells was drawn for the identification of myeloid cells. Further subsets of myeloid cell populations was achieved by establishing a gate on $CD45^{+}$/$CD4^{+}$ myeloid cell to identify monocytes and dendritic cells vs neutrophils and eosinophils. Finally, a gate (G3) was performed on $CD45^{-}$ cells to select tumor cells, erythroblasts, endothelial and mesenchymal stromal cells, where tumor cells (FIG. 1) are characterized by a $CD45^-/CD56^{+hi}/CD271^+/GD2^-/EpCAM^{-/+}/CD99^-/_{nu}$Myogenin phenotype (FIG. 1), rhabdomyosarcoma cells by a $CD45^-/CD56^{+hi}/CD271^{+hi}/GD2^-/EpCAM^-/CD99^+/_{nu}$Myogenin$^+$ profile (FIG. 2), neuroblastoma cells $CD45^-/CD56^{+hi}/CD271^{-/+/GD}2^{+hi}/EpCAM^-/CD99^-/_{nu}$Myogenin$^-$ (FIG. 3) and PNET cells $CD45^-/CD56^+/CD271^{+hi}/GD2^{+lo}/EpCAM^-/CD99^+/_{nu}$Myogenin$^-$. FIG. 3 illustrates all gating steps applied during data analysis in a bone marrow sample infiltrated by neuroblastoma cells. Table 4 shows the percentage of neoplastic cells and immune cells in the bone marrow and peripheral blood samples of all patients diagnosed with different pediatric solid tumors, as analyzed according to the present invention.

TABLE 1

Panel of antibody combination of 12/13 backbone markers in 8 or 9 distinct fluorochromes and for 14 colors combinations:

| | FLUOROCHOME POSITION | | | | | | | | | | | | | |
|---|---|---|---|---|---|---|---|---|---|---|---|---|---|---|
| | F1 e.g. BV421 | F2 e.g. BV510 | F3 e.g. BV605 | F4 e.g. BV650 | F5 e.g. BV711 | F6 e.g. BV786 | F7 e.g. FITC | F8 e.g. PerCP Cy5.5 | F9 e.g. PE | F10 e.g. PECF594 | F11 e.g. PECy7 | F12 e.g. APC | F13 e.g. AF700 | F14 e.g. APCH7 |
| 1 | cyCD3/CD271 | CD45 | — | — | — | — | CD99/CD8 | CD4/Epcam | nuMyogenin | — | CD56 | GD2 | — | smCD3/CD19 |
| 2 | cyCD3/CD271 | CD45 | — | — | — | — | CD99/CD8 | CD4/Epcam | nuMYOD1 | — | CD56 | GD2 | — | smCD3/CD19 |
| 3 | cyCD3/CD271 | CD45 | — | — | — | — | CD99/CD8 | CD4/Epcam | nuMyogenin/nuMYOD1 | — | CD56 | GD2 | — | smCD3/CD19 |
| 4 | smCD3/CD271 | CD45 | — | — | — | CD19 | CD99/CD8 | CD4/Epcam | nuMyogenin | — | CD56 | GD2 | | CyCD3 |
| 5 | smCD3/CD271 | CD45 | — | — | — | CD19 | CD99/CD8 | CD4/Epcam | nuMYOD1 | — | CD56 | GD2 | — | CyCD3 |
| 6 | smCD3/CD271 | CD45 | — | — | — | CD19 | CD99/CD8 | CD4/Epcam | nuMyogenin/nuMYOD1 | — | CD56 | GD2 | — | CyCD3 |
| 7 | cyCD3/CD271 | GD2 | — | — | — | smCD3/CD19 | CD99/CD8 | CD4/Epcam | nuMyogenin | — | CD56 | Osteopontin/BAP | CD45 | OCT3/4/PLAP |
| 8 | cyCD3/CD271 | GD2 | — | — | — | smCD3/CD19 | CD99/CD8 | CD4/Epcam | nuMYOD1 | — | CD56 | Osteopontin/BAP | CD45 | OCT3/4/PLAP |
| 9 | cyCD3/CD271 | GD2 | — | — | — | smCD3/CD19 | CD99/CD8 | CD4/Epcam | nuMyogenin | — | CD56 | Osteopontin | CD45 | OCT3/4 |
| 10 | cyCD3/CD271 | GD2 | — | — | — | smCD3/CD19 | CD99/CD8 | CD4/Epcam | nuMYOD1 | — | CD56 | Osteopontin | CD45 | OCT3/4 |
| 11 | cyCD3/CD271 | GD2 | — | CD71 | CD40 | smCD3/CD19 | CD99/CD8 | CD4/Epcam | numyogenin | — | CD56 | — | CD45 | CD30 |
| 12 | cyCD3/CD271 | GD2 | — | CD71 | CD40 | smCD3/CD19 | CD99/CD8 | CD4/Epcam | numyogenin/nuMYOD1 | — | CD56 | — | CD45 | CD30 |
| 13 | cyCD3/CD271 | GD2 | — | CD71 | CD40 | smCD3/CD19 | CD99/CD8 | CD4/Epcam | numyogenin | — | CD56 | HLADR | CD45 | CD30 |
| 14 | cyCD3/CD271 | GD2 | — | CD71 | CD40 | smCD3/CD19 | CD99/CD8 | CD4/Epcam | numyogenin/nuMYOD1 | — | CD56 | HLADR | CD45 | CD30 |
| 15 | cyCD3/CD271 | GD2 | — | — | BAP | smCD3/CD19 | CD99/CD8 | CD4/Epcam | nuMyogenin | PLAP | CD56 | Osteopontin | CD45 | OCT3/4 |
| 16 | cyCD3/CD271 | GD2 | — | — | BAP | smCD3/CD19 | CD99/CD8 | CD4/Epcam | nuMYOD1 | PLAP | CD56 | Osteopontin | CD45 | OCT3/4 |
| 17 | CD95 | GD2 | cyCD3/CD271 | CD71 | CD40 | CD19 | CD99/CD8 | CD4/Epcam | nuMYOD1 | — | CD56 | HLADR | CD45 | CD30 |
| 18 | CD95 | GD2 | smCD3/CD19 | CD30 | CD40 | cyCD3/CD271 | CD99/CD8 | CD4/Epcam | numyogenin | HLADR | CD56 | Osteopontin | CD45 | OCT3/4 |
| 19 | CD95 | GD2 | smCD3/CD19 | CD30 | CD40 | cyCD3/CD271 | CD99/CD8 | CD4/Epcam | nuMYOD1 | HLADR | CD56 | Osteopontin | CD45 | OCT3/4 |
| 20 | CD95 | GD2 | smCD3/CD19 | CD30 | CD40 | cyCD3/CD271 | CD99/CD8 | CD4/Epcam | numyogenin/nuMYOD1 | HLADR | CD56 | Osteopontin | CD45 | OCT3/4 |
| 21 | CD95 | GD2 | smCD3/CD19 | CD30 | CD40 | cyCD3/CD271 | CD99/CD8 | CD4/Epcam | nuMYOD1 | HLADR | CD56 | Osteopontin/BAP | CD45 | PLAP |
| 22 | CD95 | GD2 | smCD3/CD19 | CD30 | CD40 | cyCD3/CD271 | CD99/CD8 | CD4/Epcam | numyogenin/nuMYOD1 | HLADR | CD56 | osteopontin/BAP | CD45 | PLAP |
| 23 | CD95 | GD2 | smCD3/CD19 | CD30 | CD40 | cyCD3/CD271 | CD99/CD8 | CD4/Epcam | numyogenin | HLADR | CD56 | BAP | CD45 | PLAP |
| 24 | CD95 | GD2 | smCD3/CD19 | CD30 | CD40 | cyCD3/CD271 | CD99/CD8 | CD4/Epcam | numyogenin | HLADR | CD56 | Osteopontin/BAP | CD45 | PLAP |
| 25 | CD95 | GD2 | smCD3/CD19 | CD30 | CD40 | cyCD3/CD271 | CD99/CD8 | CD4/Epcam | numyogenin | HLADR | CD56 | BAP | CD45 | OCT3/4/PLAP |
| 26 | CD95 | GD2 | smCD3/CD19 | CD30 | CD40 | cyCD3/CD271 | CD99/CD8 | CD4/Epcam | numyogenin | HLADR | CD56 | Osteopontin/BAP | CD45 | OCT3/4/PLAP |

TABLE 1-continued

Panel of antibody combination of 12/13 backbone markers in 8 or 9 distinct fluorochromes and for 14 colors combinations:

| | FLUOROCHOME POSITION | | | | | | | | | | | | | |
|---|---|---|---|---|---|---|---|---|---|---|---|---|---|---|
| | F1 e.g. BV421 | F2 e.g. BV510 | F3 e.g. BV605 | F4 e.g. BV650 | F5 e.g. BV711 | F6 e.g. BV786 | F7 e.g. FITC | F8 e.g. PerCP Cy5.5 | F9 e.g. PE | F10 e.g. PECF594 | F11 e.g. PECy7 | F12 e.g. APC | F13 e.g. AF700 | F14 e.g. APCH7 |
| 27 | CD95 | GD2 | smCD3/ CD19 | CD30 | CD40 | cyCD3/ CD271 | CD99/ CD8 | CD4/ Epcam | nuMYOD1 | HLADR | CD56 | Osteo-pontin/ BAP | CD45 | OCT3/4/ PLAP |
| 28 | CD95 | GD2 | smCD3/ CD19 | CD30 | CD40 | cyCD3/ CD271 | CD99/ CD8 | CD4/ Epcam | numyogenin/ nuMYOD1 | HLADR | CD56 | Osteo-pontin/ BAP | CD45 | OCT3/4/ PLAP |
| 29 | CD95 | GD2 | smCD3/ CD19 | CD30 | CD40 | cyCD3/ CD271 | CD99/ CD8 | CD4/ Epcam | nuMYOD1 | HLADR | CD56 | Osteo-pontin/ BAP | CD45 | OCT3/4/ PLAP |
| 30 | CD95 | GD2 | cyCD3/ CD271 | CD71 | CD40 | CD19 | CD99/ CD8 | Epcam/ CD4 | nuMYOD1 | HLADR | CD56 | — | CD45 | CD30 |

TABLE 2

Percentage of neoplastic cells and immune cells present in tumor mass biopsies at diagnosis from pediatric cancer patients (n = 55) classified according to the tumor diagnostic subtypes.

| Tissue cell distribution(%) | % IN TOTAL CELULARITY | | | % IN TOTAL LEUCOCYTES | | | |
|---|---|---|---|---|---|---|---|
| Diagnostic group (no of samples) | Viabilitiy | Tumor cells | Immune cells | T lymphocytes | Ratio CD4:CD8 | T CD4 lymphocytes | T CD8 lymphocytes |
| HEMATOLOGICAL MALIGNANCIES | | | | | | | |
| Diffuse large B cell lymphoma (4) | 61 (39-81.6) | 30.9 (0-92.6) | 69 (7.4-100) | 54.3 (2.5-91.2) | 0.98 (0.44-1.89) | 22.4 (0.8-41.2) | 27.2 (1.5-58.3) |
| Burkitt Lymphoma (9) | 45.8 (1.1-83.9) | 60 (14.5-96.4) | 39.8 (3.6-85.5) | 72.9 (35.3-98.8) | 0.78 (0.06-2.00) | 31.3 (3.8-56) | 36.8 (10.8-67.9) |
| NON-HEMATOLOGICAL MALIGNANCIES | | | | | | | |
| Neuroblastoma and ganglioneuroblastoma (10) | 33.7 (2-92.6) | 34.8 (6-96.8) | 65.1 (3.2-94) | 48.6 (7.4-88) | 1.70 (0.51-4.13) | 21.7 (2.8-49) | 16 (1.5-39.6) |
| Nephroblastoma (10) | 37 (4.3-83.9) | 64.3 (1.5-98.3) | 34.6 (1.7-98.5) | 35.5 (13.6-67.7) | 0.56 (0.16-1.50) | 11.6 (3.3-31.7) | 22.6 (6.8-44.4) |
| Ewing tumor and related sarcomas of bone (4) | 29.5 (9.4-52.7) | 68.3 (51.8-92) | 31.6 (8-48.2) | 41.6 (10.9-73) | 0.48 (0.16-1.00) | 12.4 (1.4-31.6) | 24.9 (8.8-46.8) |
| Germ cell tumors (11) | 17.6 (6-45) | 34.3 (0.9-97.2) | 65 (2.8-99.1) | 23.9 (2.7-63.5) | 1.50 (0.51-3.80) | 11.05 (0.7-27.5) | 8.8 (1.4-25.6) |
| Nasopharyngeal carcinoma (3) | 55 (21-65) | 32 (10-69.2) | 60.4 (30.8-90) | 37 (22-46.2) | 1.05 (0.70-1.55) | 11.9 (4.2-23.4) | 12.3 (4.5-18.2) |
| Soft tissue Sarcomas* (4) | 25.8 (3.6-50) | 66.6 (11-98.4) | 33.3 (1.5-89) | 28 (14.4-64.8) | 1.70 (0.98-3.10) | 12.9 (7.1-25.9) | 9.6 (3.4-23.6) |

| Tissue cell | % IN TOTAL LEUCOCYTES | | | | | | |
|---|---|---|---|---|---|---|---|
| distribution(%) Diagnostic group (no | B | T lymphocytes | | NK | | Monocytes/ Dendritic | |
| of samples) | lymphocytes | CD56+ | CD56− | cell | Neutrophils | cells | Eosinophils |
| HEMATOLOGICAL MALIGNANCIES | | | | | | | |
| Diffuse large B cell lymphoma (4) | 5.1 (0.2-14.4) | 7.9 (0.4-28.8) | 46.3 (1.9-88.8) | 3 (0.4-7.9) | 25.8 (0.8-84.4) | 8 (1.5-18) | 2.1 (0-5.9) |

TABLE 2-continued

Percentage of neoplastic cells and immune cells present in tumor mass biopsies at diagnosis from pediatric cancer patients (n = 55) classified according to the tumor diagnostic subtypes.

| | | | | | | | |
|---|---|---|---|---|---|---|---|
| Burkitt Lymphoma (9) | 5 (0-28.1) | 3.5 (0.17-11.6) | 72.5 (23.7-97.7) | 1 (0-2.5) | 6 (0.1-31.2) | 3.2 (0-14.9) | 1.5 (0-8.9) |
| NON-HEMATOLOGICAL MALIGNANCIES | | | | | | | |
| Neuroblastoma and ganglioneuroblastoma (10) | 10.2 (0.1-36.5) | 5 (0.02-31.2) | 43.5 (6-87.8) | 2.1 (0-6.46) | 27.4 (0.93-78.7) | 13.2 (0-50.3) | 1.8 (0-8.2) |
| Nephroblastoma (10) | 3 (0-9) | 2.7 (0.05-9.6) | 33.4 (12.5-62.4) | 17.3 (1.6-65.4) | 23.9 (1.7-59.6) | 22 (2.4-41.4) | 0.9 (0-2.5) |
| Ewing tumor and related sarcomas of bone (4) | 3.8 (0.7-8.1) | 5.2 (.02-13) | 36.4 (10.9-60) | 5.8 (3-10.4) | 33.8 (7.8-60.3) | 12.5 (5.2-17.2) | 0.52 (0-1.1) |
| Germ cell tumors (11) | 2.5 (0.05-5.8) | 1.0 (0-3.1) | 22.8 (2.6-61.3) | 3.5 (0.17 13.9) | 52.2 (22.7-98) | 12.9 (1.0-39.3) | 5 (0.4-38.7) |
| Nasopharyngeal carcinoma (3) | 35 (10-54) | 2.3 (1.9-2.7) | 30.2 (20.2-40.2) | 2.4 (0.4-3.9) | 1.6 (0.6-3.3) | 3.7 (0.5-6.2) | 0.02 (0-0.04) |
| Soft tissue Sarcomas* (4) | 1.9 (1.5-2.3) | 1.7 (0.4-4.6) | 26.3 (13.2-60.2) | 4.3 (2.5-6.3) | 38.2 (14.5-65) | 24.7 (4.6-63.6) | 3.6 (0-10.2) |

*Includes two undifferentiated sarcomas, one chondrosarcoma and one clear cell sarcoma distribution(%)

TABLE 3

Percentage of neoplastic cells and the different immune cells in fluidic samples.

| Fluidic cell distribution(%) Diagnostic group (no of samples) NON- | % IN TOTAL CELULARITY | | | % IN TOTAL LEUCOCYTES | | | |
|---|---|---|---|---|---|---|---|
| HEMATOLOGICAL MALIGNANCIES | Viabilitiy | Tumor cells | Immune cells | T lymphocytes | Ratio CD4:CD8 | T CD4 lymphocytes | T CD8 lymphocytes |
| Soft tissue sarcoma (3)* | 52.6 (45.3-57.7) | 15.8 (0-47.5) | 84 (52.5-100) | 36.2 (10.5-80.2) | 1.20 (0.9-1.5) | 5.3 (4.9-5.7) | 4.6 (3.8-5.4) |
| Germ cell tumor (2) [δ] | 52.5 (25-80) | 17.4 (7.8-27) | 73 (73-92.2) | 42 (10.9-73) | 1.70 (0.84-2.7) | 15.5 (5.4-25.7) | 16.4 (2-30.8) |

| Fluidic cell distribution(%) Diagnostic group (no of samples) | % IN TOTAL LEUCOCYTES | | | | | | |
|---|---|---|---|---|---|---|---|
| NON-HEMATOLOGICAL | B | T lymphocytes | | | | Monocytes/ Dendritic | |
| MALIGNANCIES | lymphocytes | CD56+ | CD56− | NK cell | Neutrophils | cells | Eosinophils |
| Soft tissue sarcoma (3)* | 1.8 (0.6-3.8) | 1.3 (1.1-1.46) | 34.6 (9.1-78.6) | 2.1 (1.3-4.7) | 41.5 (3.8-78.1) | 17.2 (1.6-42.8) | 0 |
| Germ cell tumor (2) [δ] | 6 (0.3-11.7) | 5.4 (1.2-9.6) | 36.5 (9.7-63.4) | 6.1 (0.3-12) | 35.2 (1.5-69) | 13.3 (0.6-26) | 0.5 (0.2-0.8) |

*Includes two pleural effusion and one urine samples;

[δ] Includes, one ascitic fluid and one pleural effusion sample.

TABLE 4

Percentage of neoplastic cells and different immune cells present in bone marrow and peripheral blood samples from children diagnosed with pediatric solid tumors.

| Tissue cell distribution(%) Diagnostic group (number of samples) | % IN TOTAL CELULARITY Viabilitiy | Tumor cells | Immune cells | % IN TOTAL LEUCOCYTES T lymphocytes | Ratio CD4:CD8 | T CD4 lymphocytes | T CD8 lymphocytes |
|---|---|---|---|---|---|---|---|
| Neuroblastoma and ganglioneuroblastoma (30) | | | | | | | |
| Non-infiltrated bone marrow (13) | 84.8 (70-95) | 0 | 100 | 6 (2.3-12.1) | 1.21 (0.24-2.40) | 2.8 (0.3-5.5) | 2.4 (1.5-5.2) |
| Infiltrated bone marrow (10) | 76.6 (67-87.8) | 13.5 (0.2-41.3) | 86.4 (58.7-99.8) | 15.8 (3.7-45.3) | 1.3 (0.86-2.00) | 7.9 (1.5-22.9) | 5.6 (1.6-15.2) |
| Peripheral blood (7) | 77.4 (54.6-96.7) | 0.014 (0-0.09) | 99.8 (99-100) | 19.9 (8.2-38.63) | 1.65 (.35-4.6) | 8.9 (4-17.1) | 8.7 (2.5-20.5) |
| Ewing tumor and related sarcomas of bone (2) | | | | | | | |
| Peripheral blood (2) | 71.6 (60-83.3) | 0 | 100 | 14.3 (5.2-23.4) | 1.4 (1.3-1.5) | 7.1 (2.2-12.1) | 4.7 (1.6-7.8) |
| Rhabdomyosarcoma (1) | | | | | | | |
| Peripheral blood (1) | 78 | 0 | 100 | 5.8 | 1.69 | 3.3 | 2.0 |

| Tissue cell distribution(%) Diagnostic group (number of samples) | % IN TOTAL LEUCOCYTES B lymphocytes | T lymphocytes CD56+ | CD56− | NK cell | Neutrophils | Monocytes/ Dendritic cells | Eosinophils |
|---|---|---|---|---|---|---|---|
| Neuroblastoma and ganglioneuroblastoma (30) | | | | | | | |
| Non-infiltrated bone marrow (13) | 13.3 (0.2-51.4) | 0.04 (.01-0.1) | 6 (2.3-12.1) | 0.89 (0.2-1.6) | 50.8 (20.3-79.7) | 6.7 (2.6-12.5) | 2.8 (1.6-4) |
| Infiltrated bone marrow (10) | 9.4 (1.5-23.5) | 6.3 (0.6-28) | 9.4 (0.1-17.6) | 1.7 (0.02-7.4) | 51.7 (28.5-78.2) | 4.6 (0.6-10.4) | 2.6 (0.6-5) |
| Peripheral blood (7) | 6.4 (1.6-11.7) | 0.7 (0.01-2.7) | 17.9 (7.46-38.17) | 2.1 (0.1-8.4) | 57.8 (23.2-84.3) | 11.8 (4.01-24.4) | 1.6 (0.2-4.7) |
| Ewing tumor and related sarcomas of bone (2) | | | | | | | |
| Peripheral blood (2) | 3.9 (0.6-7.3) | 1.3 (0.5-2.2) | 12.9 (4.7-21.2) | 1.5 (1.1-2) | 74.3 (60-88.6) | 3.9 (1.9-6) | 1.8 (1.5-2.1) |
| Rhabdomyosarcoma (1) | | | | | | | |
| Peripheral blood (1) | 1.8 | 0.34 | 5.5 | 0.89 | 82.8 | 8.2 | 0.02 |

REFERENCES

Almazán-Moga A, Roma J, Molist C, Vidal I, Jubierre L, Soriano A, Segura M F, Llort A, Sánchez de Toledo J, Gallego S. Optimization of rhabdomyosarcoma disseminated disease assessment by flow cytometry. Cytometry A. 2014 December; 85(12):1020.

Bozzi F, Gambirasio F, Luksch R, Collini P, Brando B, Fossati-Bellani F. Detecting CD56+/NB84+/CD45− immunophenotype in the bone marrow of patients with metastatic neuroblastoma using flow cytometry. Anticancer Res. 2006 September-October; 26(5A):3281.

Bryson G J, Lear D, Williamson R, Wong R C. Detection of the CD56+/CD45− immunophenotype by flow cytometry in neuroendocrine malignancies. J Clin Pathol. 2002 July; 55(7):535.

Dubois S G, Epling C L, Teague J, Matthay K K, Sinclair E. Flow cytometric detection of Ewing sarcoma cells in peripheral blood and bone marrow. Pediatr Blood Cancer. 2010 January; 54(1): 13.

Ferreira-Facio C S, Milito C, Botafogo V, Fontana M, Thiago L S, Oliveira E, da Rocha-Filho A S, Werneck F, Forny D N, Dekermacher S, de Azambuja A P, Ferman S E, de Faria P A, Land M G, Orfao A, Costa E S. Contribution of multiparameter flow cytometry immunophenotyping to the diagnostic screening and classification of pediatric cancer. PLOS One. 2013; 8(3): e55534.

Magro G, Longo F R, Angelico G, Spadola S, Amore F F, Salvatorelli L. Immunohistochemistry as potential diagnostic pitfall in the most common solid tumors of children and adolescents. Acta Histochem. 2015 May-June; 117(4-5):397.

Van Dongen J J M, Orfao de Matos Correia e Vale J A, Flores-Montero J, Almeida P J M, Van der Velden V H J, Bottcher S, Rawstron A C, De Tute R M, Lhermitte L B S, Asnafi V, Mejstrikova E, Szczepanski T, Da Silva Lucio P J M, Marin Ayuso M, Pedreira C E. Methods, reagents and kits for flow cytometric immunophenotyping. US 2012/0165213 A1 June 2012.

Ward E, DeSantis C, Robbins A, Kohler B, Jemal A. Childhood and adolescent cancer statistics, 2014. CA Cancer J Clin. 2014 March-April; 64(2):83.

The invention claimed is:

1. A kit-of-parts for the flow cytometric detection of pediatric tumor cells, the kit comprising fluorochrome-conjugated antibodies directed against the cell surface markers CD45, CD56, GD2, CD99, CD8, EpCAM, CD4, smCD3, CD19 and CD271, the cytoplasmic marker cyCD3, and the nuclear marker(s) nuMyogenin and/or nuMyoD1, wherein (i) the antibodies against the markers CD99/CD8 are conjugated to the same fluorochrome and representing a first marker pair CD99/CD8;

(ii) the antibodies against the markers EpCAM/CD4 are conjugated to the same fluorochrome and representing a second marker pair EpCAM/CD4;

(ii) the antibody against CD271 is conjugated to the same fluorochrome as the antibody against either cyCD3 or smCD3 and representing a third marker pair CD271/cyCD3 or CD271/smCD3;

wherein the kit comprises antibodies conjugated to ≥8 distinguishable fluorochromes;

wherein between the first, second and third marker pairs the fluorochromes are distinguishable;

and wherein the antibodies against the cytoplasmic and the nuclear markers are physically separated from the antibodies against the cell surface markers.

2. Kit-of-parts according to claim 1, comprising a first reagent composition comprising the conjugated antibodies against the cell surface markers CD45, CD56, GD2, CD99, CD8, EpCAM, CD4, smCD3, CD19 and CD271 contained in a first container, and a second reagent composition comprising the conjugated antibodies against the cytoplasmic marker cyCD3 and the nuclear marker(s) nuMyogenin and/or nuMyoD1, contained in a second container.

3. Kit-of-parts according to claim 2, wherein the first reagent composition further comprises fluorochrome-conjugated antibodies against one or more of the Hodgkin lymphoma cell surface markers HLA-DR, CD30, CD71, CD40 and CD95.

4. Kit-of-parts according to claim 1, comprising the third marker pair CD271/cyCD3 and wherein the antibodies against the markers smCD3/CD19 are conjugated to the same fluorochrome to form a fourth marker pair smCD3/CD19, and wherein between different pairs the fluorochromes are distinguishable.

5. Kit-of-parts according to claim 1, comprising the third marker pair CD271/smCD3, and wherein the antibodies against the markers CD19 and cyCD3 are each conjugated to a distinct fluorochrome.

6. Kit-of-parts according to claim 1, comprising antibodies against the markers nuMyogenin and nuMyoD1, and wherein the antibodies against the markers nuMyogenin/nuMyoD1 are conjugated to the same fluorochrome to form a fifth marker pair nuMyogenin/nuMyoD1, and wherein between different pairs the fluorochromes are distinguishable.

7. Kit-of-parts according to claim 1, further comprising fluorochrome-conjugated antibodies against one or more of the germ cell tumor cell surface markers OCT-3/4, BAP and PLAP.

8. Kit-of-parts according to claim 7, comprising antibodies against the markers OCT-3/4 and PLAP, and wherein the antibodies against the markers OCT-3/4/PLAP are conjugated to the same fluorochrome to form a marker pair OCT-3/4/PLAP, and wherein between different pairs the fluorochromes are distinguishable.

9. Kit-of-parts according to claim 1, further comprising fluorochrome-conjugated antibodies against one or more of the bone tumor cell surface markers osteopontin and bone alkaline phosphatase.

10. Kit-of-parts according to claim 9, comprising antibodies against the markers osteopontin and bone alkaline phosphatase referred to as BAP, and wherein the antibodies against the markers osteopontin/BAP are conjugated to the same fluorochrome to form a marker pair osteopontin/BAP, and wherein between different pairs the fluorochromes are distinguishable.

11. Kit-of-parts according to claim 1, further comprising a nucleated cell integrity dye.

12. Kit-of-parts according to claim 1, further comprising reagents for fixing and permeabilizing cells, optionally together with instructions for use, buffer, and/or control samples.

13. A multi-color flow cytometric method for identification and classification of pediatric tumors, comprising the steps of:

(a) Staining an aliquot of a biological sample comprising or suspected to comprise childhood tumor cells with the fluorochrome-conjugated antibodies against cell surface markers as comprised in a kit-of-part according to claim 1; followed by (b) Contacting the stained cells with a fixation solution, followed by (c) permeabilizing the fixed and stained cells with a permeabilizing solution; followed by (d) staining the permeabilized cells with the fluorochrome-conjugated antibodies against cytoplasmic and nuclear markers as comprised in a kit-of-part according to claim 1;

(e) analyzing the stained cells in said aliquot in a flow cytometer; and (f) storing and evaluating the data obtained.

14. The method according to claim 13, wherein the biological sample is a primary tumor tissue sample, peripheral blood, bone marrow, tissue sample comprising one of lymph nodes, adenoid, spleen, or liver, or other type of body fluid comprising one of cerebrospinal fluid, vitreous fluid, synovial fluid, final needle aspirate, pleural effusions or ascites, said sample being obtained from a pediatric patient.

15. The method according to claim 13, further comprising selecting an appropriate targeted therapy.

16. The method of claim 13 wherein the evaluating of the data obtained is used in the diagnosis and classification of one or more pediatric tumors, preferably selected from: i) neuroectodermal neoplasias; ii) tumors with myofibroblastic cell differentiation; iii) identification of commitment into multiple cell lineages; and iv) T and B-lymphoblastic lymphoma/leukemia.

17. An antibody panel for the flow cytometric detection of pediatric tumor cells, the combination comprising fluorochrome-conjugated antibodies directed against the cell surface markers CD45, CD56, GD2, CD99, CD8, EpCAM, CD4, smCD3, CD19 and CD271, the cytoplasmic marker cyCD3, and the nuclear marker(s) nuMyogenin and/or nuMyoD1, wherein (i) the antibodies against the markers CD99/CD8 are conjugated to the same fluorochrome and representing a first marker pair CD99/CD8;

(ii) the antibodies against the markers EpCAM/CD4 are conjugated to the same fluorochrome and representing a second marker pair EpCAM/CD4;

(ii) the antibody against CD271 is conjugated to the same fluorochrome as the antibody against either cyCD3 or smCD3 and representing a third marker pair CD271/cyCD3 or CD271/smCD3;

wherein the antibody panel comprises antibodies conjugated to ≥8 distinguishable fluorochromes; wherein between the first, second and third marker pairs the fluorochromes are distinguishable; and wherein the antibodies against the cytoplasmic and the nuclear markers are physically separated from the antibodies against the cell surface markers.

* * * * *